United States Patent
Kuroda et al.

(10) Patent No.: US 12,396,634 B2
(45) Date of Patent: Aug. 26, 2025

(54) MEDICAL OBSERVATION DEVICE, OBSERVATION DEVICE, OBSERVATION METHOD, AND ADAPTER

(71) Applicant: SONY GROUP CORPORATION, Tokyo (JP)

(72) Inventors: Yohei Kuroda, Tokyo (JP); Shinji Katsuki, Tokyo (JP); Kei Tomatsu, Tokyo (JP); Yugo Katsuki, Tokyo (JP); Daisuke Nagao, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 18/264,385

(22) PCT Filed: Jan. 21, 2022

(86) PCT No.: PCT/JP2022/002276
§ 371 (c)(1),
(2) Date: Aug. 4, 2023

(87) PCT Pub. No.: WO2022/172733
PCT Pub. Date: Aug. 18, 2022

(65) Prior Publication Data
US 2024/0090759 A1   Mar. 21, 2024

(30) Foreign Application Priority Data
Feb. 12, 2021 (JP) ................. 2021-020822

(51) Int. Cl.
*A61B 1/313* (2006.01)
*A61B 1/00* (2006.01)
*H04N 25/47* (2023.01)

(52) U.S. Cl.
CPC ........ *A61B 1/3132* (2013.01); *A61B 1/00179* (2013.01); *H04N 25/47* (2023.01)

(58) Field of Classification Search
CPC .............. A61B 1/3132; A61B 1/00179; A61B 1/000095; A61B 1/042; A61B 1/045; H04N 25/47; H04N 23/555
(Continued)

(56) References Cited

U.S. PATENT DOCUMENTS

2011/0292258 A1* 12/2011 Adler ................. H10F 39/8053
348/263
2013/0038708 A1* 2/2013 Iwasaki ............. A61B 1/00188
348/E7.085
(Continued)

FOREIGN PATENT DOCUMENTS

EP       3090680 B1    5/2020
JP    2020-025263 A    2/2020
(Continued)

OTHER PUBLICATIONS

International Search Report and Written Opinion of PCT Application No. PCT/JP2022/002276, issued on Apr. 12, 2022, 09 pages of ISRWO.

*Primary Examiner* — Marnie A Matt
(74) *Attorney, Agent, or Firm* — CHIP LAW GROUP

(57) ABSTRACT

There is provided a medical observation device that includes an imaging unit that can image an environment inside an abdominal cavity of a living body, and the imaging unit includes a plurality of first pixels that are aligned in a matrix, and an event detection unit that detects a luminance change amount of light incident on each of the plurality of first pixels exceeds a predetermined threshold.

19 Claims, 20 Drawing Sheets

(58) Field of Classification Search
USPC .......................................................... 348/68
See application file for complete search history.

(56) References Cited

U.S. PATENT DOCUMENTS

| | | | |
|---|---|---|---|
| 2016/0000307 A1* | 1/2016 | Akimoto | A61B 1/000094 |
| | | | 600/109 |
| 2016/0094796 A1* | 3/2016 | Govil | H04N 25/707 |
| | | | 348/295 |
| 2018/0295298 A1* | 10/2018 | Zamir | H04N 25/533 |
| 2018/0344284 A1* | 12/2018 | Freudenberger | G06N 3/045 |
| 2019/0043583 A1* | 2/2019 | Majumder | G11C 15/04 |
| 2019/0167377 A1* | 6/2019 | Hirose | G02B 21/0012 |
| 2020/0160813 A1* | 5/2020 | Aurongzeb | G09G 3/36 |
| 2020/0315432 A1 | 10/2020 | Tully | |
| 2020/0410272 A1* | 12/2020 | Seo | G06V 10/22 |
| 2021/0152757 A1* | 5/2021 | Wakabayashi | H04N 25/51 |
| 2022/0150424 A1* | 5/2022 | Numata | H04N 25/47 |
| 2022/0172375 A1* | 6/2022 | Seo | H04N 25/46 |
| 2023/0300282 A1* | 9/2023 | Seo | H04N 25/00 |
| | | | 348/294 |

FOREIGN PATENT DOCUMENTS

| | | |
|---|---|---|
| JP | 2020-127186 A | 8/2020 |
| WO | 2016/129160 A1 | 8/2016 |
| WO | 2016/129162 A1 | 8/2016 |
| WO | WO-2020116185 A1 | 6/2020 |

* cited by examiner

MEDICAL OBSERVATION DEVICE, OBSERVATION DEVICE, OBSERVATION METHOD, AND ADAPTER

CROSS REFERENCE TO RELATED APPLICATIONS

This application is a U.S. National Phase of International Patent Application No. PCT/JP2022/002276 filed on Jan. 21, 2022, which claims priority benefit of Japanese Patent Application No. JP 2021-020822 filed in the Japan Patent Office on Feb. 12, 2021. Each of the above-referenced applications is hereby incorporated herein by reference in its entirety.

FIELD

The present disclosure relates to a medical observation device, an observation device, an observation method, and an adapter.

BACKGROUND

In recent years, in endoscopic surgery, surgery is performed while imaging an inside of an abdominal cavity of a patient using an endoscope, and displaying on a display the captured image imaged by the endoscope. For example, following Patent Literature 1 and following Patent Literature 2 disclose techniques of endoscopes.

CITATION LIST

Patent Literature

Patent Literature 1: WO 2016/129162 A
Patent Literature 2: WO 2016/129160 A

SUMMARY

Technical Problem

However, the above-described conventional techniques have limits in robustly and highly accurately measuring and recognizing in real time a subject such as an environment inside an abdominal cavity having a restriction.

Therefore, the present disclosure proposes a medical observation device, an observation device, an observation method, and an adapter that enable real-time, robust, and highly accurate measurement and recognition of a subject.

Solution to Problem

According to the present disclosure, there is provided a medical observation device including an imaging unit that can image an environment inside an abdominal cavity of a living body. In the medical observation device, the imaging unit includes: a plurality of first pixels that are aligned in a matrix, and an event detection unit that detects that a luminance change amount of light incident on each of the plurality of first pixels exceeds a predetermined threshold.

Furthermore, according to the present disclosure, there is provided an observation device including: an imaging unit; and an image detection unit. In the observation device, the imaging unit includes a plurality of first pixels that are aligned in a matrix, and an event detection unit that detects that a luminance change amount of light incident on each of the plurality of first pixels exceeds a predetermined threshold. The image detection unit includes a plurality of second pixels that are aligned in a matrix, and detects an image that is based on the light incident on each of the plurality of second pixels.

Furthermore, according to the present disclosure, there is provided an observation method includes: by a medical observation device that can image an environment inside an abdominal cavity of a living body, detecting luminance of light incident on each of a plurality of first pixels aligned in a matrix; calculating a change amount of the luminance; and determining whether or not the change amount exceeds a predetermined threshold.

Furthermore, according to the present disclosure, there is provided an adapter includes: a plurality of second pixels aligned in a matrix, and is inserted between a camera head unit and an optical system, the camera head unit includes an image detection unit that detects an image that is based on light incident on each of the plurality of second pixels, and the optical system guides the light to the camera head unit. The adapter includes an imaging unit that can image an environment inside an abdominal cavity of a living body. In the adapter, the imaging unit includes: a plurality of first pixels that are aligned in a matrix, and an event detection unit that detects that a luminance change amount of light incident on each of the plurality of first pixels exceeds a predetermined threshold.

DESCRIPTION OF EMBODIMENTS

Figure 1:
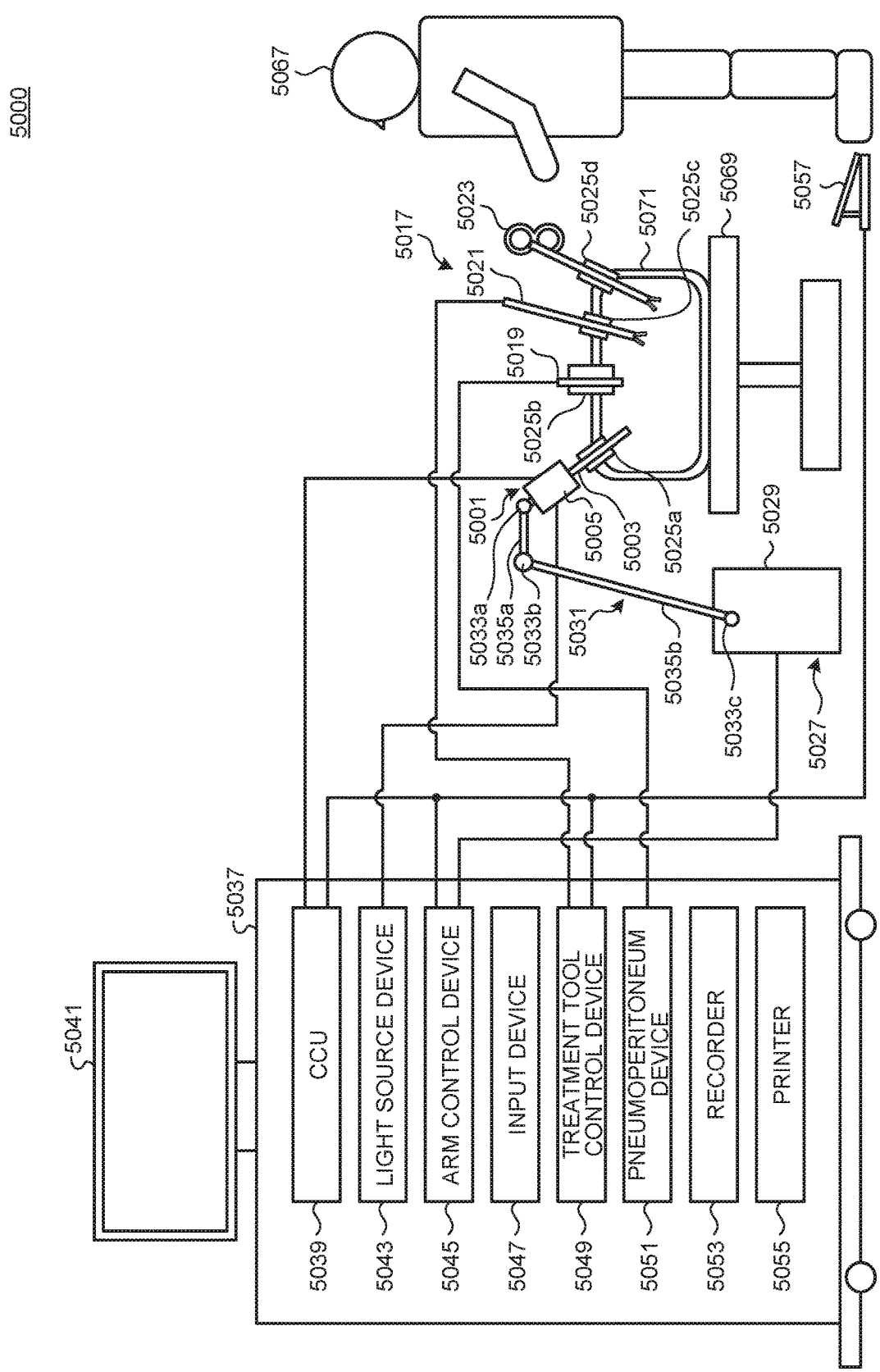
FIG. 1 is a diagram illustrating an example of a schematic configuration of an endoscopic surgery system to which a technique according to the present disclosure is applicable.

Hereinafter, preferred embodiments of the present disclosure will be described in detail with reference to the accompanying drawings. Note that, in the description and the drawings, components employing substantially the same functional configurations will be assigned the same reference numerals, and redundant description will be omitted. Furthermore, in the description and the drawings, a plurality of components employing substantially the same or similar functional configurations are distinguished by assigning different alphabets to ends of the same reference numerals in some cases. In this regard, in a case where it is not particularly necessary to distinguish each of a plurality of components employing substantially the same or similar functional configurations, only the same reference numeral is assigned.

Note that the description will be given in the following order.

1. Configuration Example of Endoscopic Surgery System 5000
1.1 Schematic Configuration of Endoscopic Surgery System 5000
1.2 Detailed Configuration Example of Support Arm Device 5027
1.3 Detailed Configuration Example of Light Source Device
2. Background Leading to Creation of Embodiments of Present Disclosure
2.1 Background Leading to Creation of Embodiments of Present Disclosure
2.2 Outline of Embodiments of Present Disclosure
2.3 Regarding EVS
3. First Embodiment
3.1 Configuration Example of Medical Observation System 10
3.2 Configuration Example of Camera Head 100 and Optical System 400
3.3 Functional Block Configuration Example
3.4 Control Method
3.5 Modified Example
4. Second Embodiment
5. Third Embodiment
6. Fourth Embodiment
6.1 First Example
6.2 Second Example
7. Fifth Embodiment
8. Conclusion
9. Hardware Configuration
10. Supplementary Note 1. Configuration Example of Endoscopic Surgery System 5000

1.1 Schematic Configuration of Endoscopic Surgery System 5000

First, prior to description of details of embodiments of the present disclosure, a schematic configuration of the endoscopic surgery system 5000 to which a technique according to the present disclosure can be applied will be described with reference to FIG. 1. FIG. 1 is a diagram illustrating an example of the schematic configuration of the endoscopic surgery system 5000 to which the technique according to the present disclosure can be applied. FIG. 1 illustrates a state where a surgeon 5067 is performing surgery on a patient 5071 on a patient bed 5069 using the endoscopic surgery system 5000. As illustrated in FIG. 1, the endoscopic surgery system 5000 includes an endoscope 5001, other surgical instruments 5017, the support arm device 5027 that supports the endoscope 5001, and a cart 5037 on which various devices for endoscopic surgery are mounted. Hereinafter, details of the endoscopic surgery system 5000 will be sequentially described.

(Surgical Instrument 5017)

According to endoscopic surgery, for example, a plurality of cylindrical specula that are called trocars 5025a to 5025d puncture an abdominal wall instead of cutting the abdominal wall and performing laparotomy. Furthermore, a lens barrel 5003 of the endoscope 5001 and the other surgical instrument 5017 are inserted from the trocars 5025a to 5025d into a body cavity of the patient 5071. In the example illustrated in FIG. 1, a pneumoperitoneum tube 5019, an energy treatment tool 5021, and forceps 5023 are inserted as the other surgical instruments 5017 into the body cavity of the patient 5071. Furthermore, the energy treatment tool 5021 is a treatment tool that, for example, incises and detaches tissues, and seals blood vessels by a high frequency current or ultrasonic vibration. In this regard, the surgical instrument 5017 illustrated in FIG. 1 is merely an example, and examples of the surgical instruments 5017 include various surgical instruments such as tweezers and retractors that are generally used for endoscopic surgery.

(Support Arm Device 5027)

The support arm device 5027 includes an arm part 5031 that extends from a base part 5029. In the example illustrated in FIG. 1, the arm part 5031 includes joint parts 5033a, 5033b, and 5033c, and links 5035a and 5035b, and is driven under control of an arm control device 5045. Furthermore, the endoscope 5001 is supported by the arm part 5031 to control a position and a posture of the endoscope 5001. Consequently, it is possible to stably fix the position of the endoscope 5001.

(Endoscope 5001)

The endoscope 5001 includes the lens barrel 5003 whose area of a predetermined length from a distal end is inserted into the body cavity of the patient 5071, and a camera head 5005 that is connected to a proximal end of the lens barrel 5003. Although the example illustrated in FIG. 1 illustrates the endoscope 5001 configured as a so-called rigid endoscope including the rigid lens barrel 5003, the endoscope 5001 may be configured as a so-called flexible endoscope having the flexible lens barrel 5003, and is not particularly limited in the embodiments of the present disclosure.

An opening part into which an objective lens is fitted is provided at the distal end of the lens barrel 5003. The endoscope 5001 is connected with the light source device (medical light source device) 5043, and light generated by the light source device 5043 is guided to the distal end of the lens barrel by a light guide extending to an inside of the lens barrel 5003, and is radiated toward an observation target in the body cavity (e.g., an inside of the abdominal cavity) of the patient 5071 through the objective lens. Note that, in the embodiments of the present disclosure, the endoscope 5001 may be a forward viewing endoscope, or may be an oblique viewing endoscope, and is not particularly limited.

An optical system and an imaging element are provided inside the camera head 5005, and reflected light (observation light) from the observation target is condensed on the imaging element by the optical system. The observation light is photoelectrically converted by the imaging element to generate an electric signal corresponding to the observation light, that is, a pixel signal corresponding to an observation image. The pixel signal is transmitted as RAW data to a Camera Control Unit (CCU) 5039. Note that a function of adjusting a magnification and a focal distance by appropriately driving this optical system is mounted on the camera head 5005.

Note that, for example, a plurality of imaging elements may be provided in the camera head 5005 to support stereoscopic vision (stereoscopic system) or the like. In this case, a plurality of relay optical systems are provided inside the lens barrel 5003 to guide the observation light to each of the plurality of imaging elements. Furthermore, different types of imaging elements can be provided in the embodiments of the present disclosure, which will be described later. Furthermore, details of the camera head 5005 and the lens barrel 5003 according to the embodiments of the present disclosure will also be described later.

(Various Devices Mounted on Cart)

First, under control of the CCU 5039, a display device 5041 displays an image that is based on a pixel signal subjected to image processing by the CCU 5039. In a case where the endoscope 5001 supports high resolution photographing such as 4K (3840 horizontal pixels×2160 vertical pixels) or 8K (7680 horizontal pixels×4320 vertical pixels), and/or supports 3D display, for example, a display device that can perform high resolution display corresponding to each of 4K and 8K and/or a display device that can perform 3D display is used as the display device 5041. Furthermore, the plurality of display devices 5041 having different resolutions and sizes may be provided depending on applications.

Furthermore, an image of a surgical site inside the body cavity of the patient 5071 photographed by the endoscope 5001 is displayed on the display device 5041. While viewing the image of the surgical site displayed on the display device 5041 in real time, the surgeon 5067 can perform treatment such as excision of an affected part using the energy treatment tool 5021 and the forceps 5023. Note that, although not illustrated, the pneumoperitoneum tube 5019, the energy treatment tool 5021, and the forceps 5023 may be supported by the surgeon 5067, an assistant, or the like during surgery.

Furthermore, the CCU 5039 includes a Central Processing Unit (CPU), a Graphics Processing Unit (GPU), and the like, and can integrally control operations of the endoscope 5001 and the display device 5041. More specifically, the CCU 5039 performs various image processing such as development processing (demosaic processing) for displaying an image that is based on the pixel signal, on the pixel signal accepted from the camera head 5005. Furthermore, the CCU 5039 provides the pixel signal subjected to the image processing to the display device 5041. Furthermore, the CCU 5039 transmits a control signal to the camera head 5005, and controls driving of the camera head 5005. The control signal can include information that relates to imaging conditions such as a magnification and a focal distance. Note that details of the CCU 5039 according to the embodiments of the present disclosure will be described later.

The light source device 5043 includes a light source such as a Light Emitting Diode (LED), and supplies irradiation light for photographing a surgical site to the endoscope 5001. Note that details of the light source device 5049 according to the embodiments of the present disclosure will be described later.

The arm control device 5045 includes, for example, a processor such as a CPU, and operates according to a predetermined program to control driving of the arm part 5031 of the support arm device 5027 according to a predetermined control scheme. Note that details of the arm control device 5045 according to the embodiments of the present disclosure will be described later.

An input device 5047 is an input interface for the endoscopic surgery system 5000. The surgeon 5067 can input various pieces of information and input instructions to the endoscopic surgery system 5000 via the input device 5047. For example, the surgeon 5067 inputs various pieces of information related to surgery such as body information of a patient and information regarding a surgical procedure of the surgery via the input device 5047. Furthermore, for example, the surgeon 5067 can input an instruction to drive the arm part 5031, an instruction to change imaging conditions (a type of irradiation light, a magnification, a focal distance, and the like) of the endoscope 5001, an instruction to drive the energy treatment tool 5021, and the like via the input device 5047. Note that the type of the input device 5047 is not limited, and the input device 5047 may be various known input devices. As the input device 5047, for example, a mouse, a keyboard, a touch panel, a switch, a foot switch 5057, a lever, and/or the like can be applied. In a case where, for example, the touch panel is used as the input device 5047, the touch panel may be provided on a display surface of the display device 5041.

Alternatively, the input device 5047 may be a device such as an eyeglass-type wearable device or a Head Mounted Display (HMD) that is attached to part of the body of the surgeon 5067. In this case, various inputs are performed according to gestures or lines of sight of the surgeon 5067 detected by these devices. Furthermore, the input device 5047 can include a camera that can detect motions of the surgeon 5067, and may input various inputs according to gestures or lines of sight of the surgeon 5067 detected from images imaged by the camera. Furthermore, the input device 5047 can include a microphone that can collect voice of the surgeon 5067, and may input various inputs with voice via the microphone. As described above, the input device 5047 is configured to be able to input various pieces of information in a non-contact manner, so that a user (e.g., the surgeon 5067) belonging to a clean area in particular can operate equipment belonging to an unclean area in a non-contact manner. Furthermore, the surgeon 5067 can operate the equipment without releasing a possessed surgical instrument from the hand, so that convenience of the surgeon 5067 improves.

A treatment tool control device 5049 controls driving of the energy treatment tool 5021 for cauterization and incision of tissues, sealing of blood vessels, or the like. A pneumoperitoneum device 5051 feeds gas into the body cavity of the patient 5071 through the pneumoperitoneum tube 5019 to inflate the body cavity for a purpose of securing a visual field of the endoscope 5001 and securing a working space of the surgeon 5067. A recorder 5053 is a device that can record various pieces of information related to surgery. A printer 5055 is a device that can print various pieces of information related to surgery in various formats such as a text, an image, or a graph.

1.2 Detailed Configuration Example of Support Arm Device 5027

Furthermore, an example of a detailed configuration of the support arm device 5027 will be described. The support arm device 5027 includes the base part 5029 that is a base, and the arm part 5031 that extends from the base part 5029. Although the arm part 5031 includes the plurality of joint parts 5033a, 5033b, and 5033c, and the plurality of links 5035a and 5035b coupled by the joint part 5033b in the example illustrated in FIG. 1, FIG. 1 illustrates a simplified configuration of the arm part 5031 for the sake of simplicity. More specifically, the shape, the number, and arrangement of the joint parts 5033a to 5033c and the links 5035a and 5035b, a direction of rotation axes of the joint parts 5033a to 5033c, and the like can be appropriately set such that the arm part 5031 has a desired degree of freedom. For example, the arm part 5031 can be suitably configured to have a degree of freedom equal to or more than six degrees of freedom. Consequently, it is possible to freely move the endoscope 5001 within a movable range of the arm part 5031, so that the lens barrel 5003 of the endoscope 5001 can be inserted into the body cavity of the patient 5071 from a desired direction.

Actuators are provided to the joint parts 5033a to 5033c, and the joint parts 5033a to 5033c are configured to be able to rotate around a predetermined rotation axis by driving the actuators. Driving of the actuators is controlled by the arm control device 5045 to control a rotation angle of each of the joint parts 5033a to 5033c, and control driving of the arm part 5031. Consequently, it is possible to realize control of a position and a posture of the endoscope 5001. At this time, the arm control device 5045 can control driving of the arm part 5031 by various known control schemes such as force control or position control.

For example, the surgeon 5067 may appropriately input an operation via the input device 5047 (including the foot switch 5057) to make the arm control device 5045 appropriately control driving of the arm part 5031, and control the position and the posture of the endoscope 5001 according to the operation input. Note that the arm part 5031 may be operated by a so-called master-slave mode. In this case, the arm part 5031 (slave) can be remotely controlled by the surgeon 5067 via the input device 5047 (master console) installed at a place remote from an operation room or in the operating room.

Here, doctors who are called scopists have generally supported the endoscope 5001 for endoscopic surgery. By contrast with this, according to the embodiments of the present disclosure, it is possible to reliably fix the position of the endoscope 5001 without someone else's hand by using the support arm device 5027, so that it is possible to stably obtain an image of a surgical site, and smoothly perform surgery.

Note that the arm control device 5045 may not necessarily be provided to the cart 5037. Furthermore, the arm control device 5045 may not necessarily be one device. For example, the arm control device 5045 may be each provided to each of the joint parts 5033a to 5033c of the arm part 5031 of the support arm device 5027, and the plurality of arm control devices 5045 may cooperate with each other to realize driving control of the arm part 5031.

1.3 Detailed Configuration Example of Light Source Device 5043

Next, the example of the detailed configuration of the light source device 5043 will be described. The light source device 5043 supplies to the endoscope 5001 irradiation light for photographing a surgical site. The light source device 5043 includes, for example, white light sources formed by LEDs, laser light sources, or a combination of these. At this time, in a case where the white light sources are formed by a combination of RGB laser light sources, it is possible to highly accurately control an output intensity and an output timing of each color (each wavelength), so that the light source device 5043 can adjust a white balance of a captured image. Furthermore, in this case, by irradiating an observation target with the laser light from each of the RGB laser light sources in a time division manner, and controlling driving of the imaging element of the camera head 5005 in synchronization with an irradiation timing of the laser light, it is also possible to image an image corresponding to each of RGB in the time division manner. According to this method, it is possible to obtain a color image without providing a color filter to the imaging element.

Furthermore, driving of the light source device 5043 may be controlled to change an intensity of light to be output per predetermined time. By controlling driving of the imaging element of the camera head 5005 in synchronization with a timing to change the intensity of the light, acquiring images in the time division manner, and synthesizing the images, it is possible to generate an image of a high dynamic range without so-called blocked up shadows and over exposure.

Furthermore, the light source device 5043 may be configured to be able to supply light of a predetermined wavelength band corresponding to special light imaging. Special light imaging performs so-called narrow band imaging for radiating light of a narrower band than that of irradiation light (i.e., white light) at a time of normal observation using wavelength dependency of light absorption in body tissues, and thereby photographing predetermined tissues such as blood vessels in a mucosal surface layer with high contrast. Alternatively, special light imaging may perform fluorescence imaging for obtaining an image using fluorescence generated by radiating excitation light. According to fluorescence imaging, body tissues may be irradiated with excitation light to observe fluorescence from the body tissues (autofluorescence imaging), or a reagent such as Indocyanine Green (ICG) may be locally injected into body tissues and the body tissues may be irradiated with excitation light corresponding to a fluorescence wavelength of the reagent to obtain a fluorescent image. The light source device 5043 can be configured to be able to supply narrow band light and/or excitation light that support such special light imaging.

2. Background Leading to Creation of Embodiments of Present Disclosure

2.1 Background Leading to Creation of Embodiments of Present Disclosure

Meanwhile, in recent years, development for causing the support arm device 5027 to autonomously operate has been advanced for the above-described endoscopic surgery system 5000. More specifically, the autonomous operation of the support arm device 5027 in the endoscopic surgery system 5000 can be classified into various levels. Examples of the levels include a level at which the surgeon (operator) 5067 is guided by the system, and a level at which the system autonomously executes part of operations (tasks) of surgery of, for example, suturing a surgical site by moving a position of the endoscope 5001 and causing the surgical instrument 5017 to autonomously operate. Furthermore, the examples of the levels can include, for example, a level at which the system automatically generates operation contents of the surgery, and the endoscopic surgery system 5000 performs an operation selected by a doctor from the automatically generated operation. Furthermore, a level at which the endoscopic surgery system 5000 executes all tasks of surgery under monitoring of the doctor or without monitoring of the doctor in the future may also be conceivable.

Note that the embodiments of the present disclosure described below assume use in a case where the endoscopic surgery system 5000 autonomously executes a task (scope work) of moving the position of the endoscope 5001 in place of a scopist, and the surgeon 5067 performs surgery directly or surgery by a remote operation by referring to an image obtained by the moved endoscope 5001. According to endoscopic surgery, for example, depending on a difference in skill of scope work of an assistant who operates an endoscope, an appropriate field of view cannot be obtained, a surgical result is affected, moreover, there are problems of difficulty of the skill of the scope work itself and a shortage of medical workers due to aging, and therefore it is strongly demanded to make the scope work of the endoscopic surgery system 5000 autonomous.

For this purpose, for example, it is required to robustly measure and recognize the environment inside an abdominal cavity in real time, and cause the endoscopic surgery system 5000 to autonomously operate based on a recognition result. However, although conventional techniques mainly use the endoscope 5001 that uses an RGB sensor that is a sensor that detects light of three primary colors of red (R), green (G), and blue (B), such an RGB sensor has had a limit in robustly and highly accurately measuring and recognizing a laparoscopic environment in real time.

Figure 2:
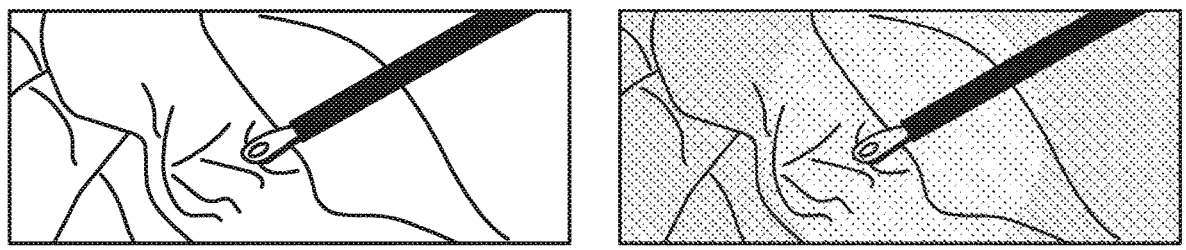
FIG. 2 is a view illustrating an example of an image of a laparoscopic environment.

Referring to, for example, FIG. 2 illustrating an example of an image of an inside of an abdominal cavity, the RGB sensor is expected to acquire an image as illustrated on the left side of FIG. 2. However, the abdominal cavity is actually a closed environment, a light irradiation range of the endoscopic surgery system 5000 is also limited, and therefore the RGB sensor can only acquire a dark image as illustrated on the right side of FIG. 2 depending on conditions in some cases. Such a dark image makes it difficult to accurately recognize a tumor, a surgical site, or a surgical instrument inside an abdominal cavity from, for example, the image, and, for example, it is difficult to acquire an image of a desired site, recognize the surgical site, and avoid an interference with the surgical instrument. Furthermore, when an imaging target becomes dark, it is necessary to reduce a shutter speed, and, when a surgical site moves or deforms, motion blur remarkably occurs in an image, which may make recognition more difficult.

Furthermore, a large difference between brightness and darkness is likely to occur in environment inside an abdominal cavity, and therefore it is difficult to recognize a subject (e.g., a tumor, a surgical site, a surgical instrument, or the like) captured at a dark part of an image. Furthermore, it is difficult to recognize organs having no characteristic texture or parts to which blood is attached even if these organs and parts are segmented, and a high frame rate is required to capture high speed deformation of the organ, and therefore a processing load is great, that is, the environment inside the abdominal cavity has many disadvantageous conditions for recognition processing that uses an RGB sensor.

Furthermore, although it is conceivable to use not only an RGB sensor, but also a distance measurement device of, for example, a Time of Flight (ToF) scheme that performs distance measurement using a return time of reflection of pulsed light from a subject to measure and recognize the environment inside the abdominal cavity, there are many problems that, for example, water, a body fluid, a blood, or the like make it difficult to perform accurate distance measurement due to specular reflection on a liquid surface thereof unique to surgery environment in a case where the ToF is used, and, moreover, it is difficult to incorporate the distance measurement device into the endoscope 5001.

2.2 Outline of Embodiments of Present Disclosure

Furthermore, in the above-described situation, the inventors of the present disclosure have intensively studied means for robustly measuring and recognizing an environment inside an abdominal cavity in real time. During such study, the inventors of the present disclosure have reached an idea that it is possible to compensate for drawbacks of existing RGB sensors using an Event Vision Sensor (EVS).

The EVS is an image sensor that sensitively detects a luminance change, and has higher sensitivity than that of general RGB sensors. Consequently, it is possible to easily obtain a shape (edge information) of a subject even in a dark place that is difficult for the RGB sensor to capture.

Furthermore, the EVS has no concept of a frame rate, and can sparsely output time stamp information and pixel information when a luminance change exceeds a threshold. Consequently, the EVS can output the time stamp information and the pixel information at a high frame rate in response to frequent luminance changes. Furthermore, by integrating outputs of a certain period from the EVS, and converting the outputs as an image of a suitable frame rate, it is possible to easily capture a motion and deformation of the subject. More specifically, the number of events to be integrated changes according to a frame length, and therefore the information included in the converted image also changes. Consequently, by performing processing of adjusting the frame length to capture a desired subject and deformation thereof using such features of the EVS, it is possible to more easily obtain the shape (edge information) of the subject, and improve recognition performance of the subject.

Furthermore, the EVS does not output all pixel information every other certain frames, and therefore a data amount becomes smaller than that of a normal RGB sensor, so that it is possible to make a load of arithmetic processing lower.

According to the embodiments of the present disclosure that are created by the inventors of the present disclosure and use the above-described EVS, it is possible to robustly measure and recognize an environment inside an abdominal cavity in real time. Furthermore, according to the embodiments of the present disclosure, it is possible to robustly and highly accurately measure and recognize the environment inside the abdominal cavity in real time, so that it is also easy to make scope work of the endoscopic surgery system 5000 autonomous. In addition, according to the embodiments of the present disclosure, advantages of conventional image recognition such as tracking of long term feature that the RGB camera is good at, and the EVS are combined, so that it is possible to more robustly measure and recognize the environment inside an abdominal cavity in more real time. Hereinafter, details of these embodiments of the present disclosure will be sequentially described.

2.3 Regarding EVS

Figure 3:
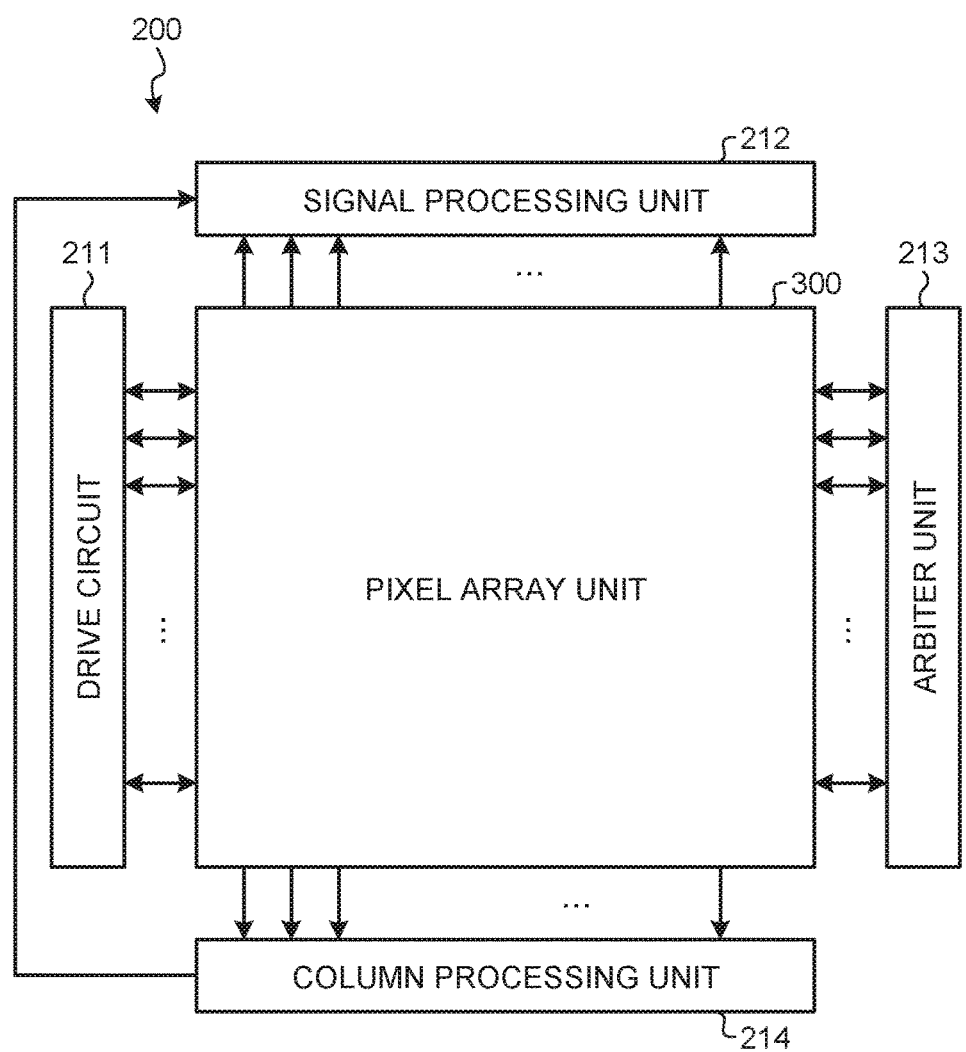
FIG. 3 is a block diagram illustrating an example of a configuration of an EVS 200 used in embodiments of the present disclosure.
Figure 4:
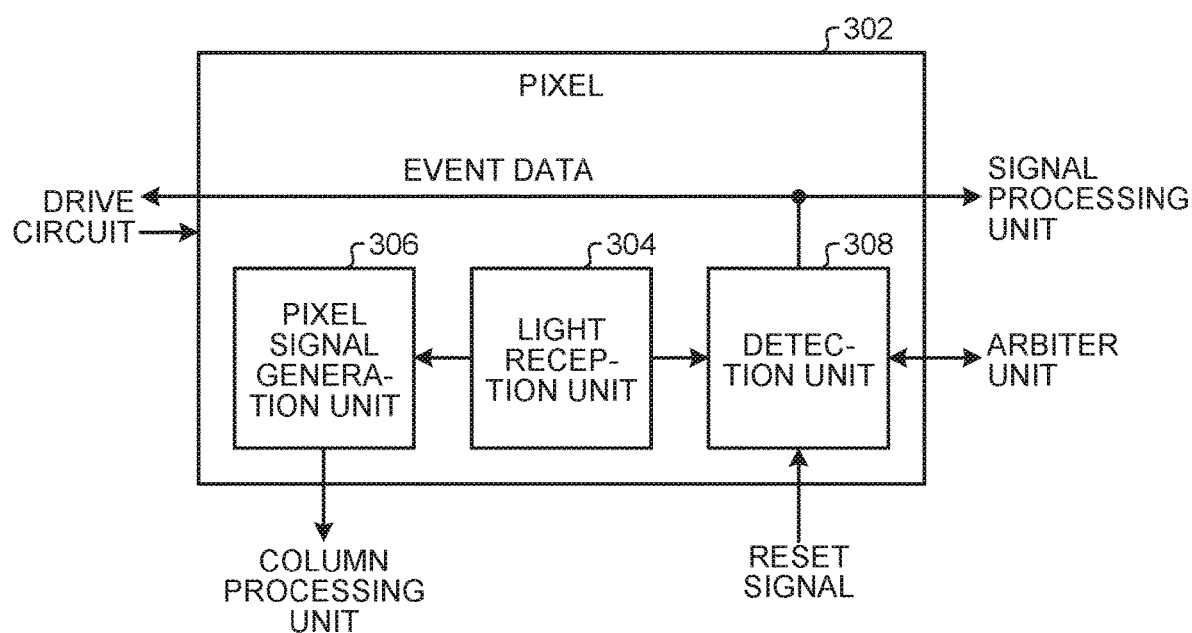
FIG. 4 is a block diagram illustrating an example of a configuration of a pixel 302 located in a pixel array unit 300 in the EVS 200 illustrated in FIG. 3.

Here, the Event Vision Sensor (EVS) will be described with reference to FIGS. 3 and 4. FIG. 3 is a block diagram illustrating an example of a configuration of an EVS 200 used in the embodiments of the present disclosure, and FIG. 4 is a block diagram illustrating an example of a configuration of a pixel 302 located in a pixel array unit 300 in the EVS 200 illustrated in FIG. 3.

As illustrated in FIG. 3, the EVS 200 includes the pixel array unit 300 configured by aligning the plurality of pixels (first pixels) 302 (see FIG. 4) in a matrix. Each pixel 302 can generate as a pixel signal a voltage corresponding to a photocurrent generated by photoelectric conversion. Furthermore, each pixel 302 can detect whether or not an event has occurred by comparing with a predetermined threshold a change in the photocurrent corresponding to a change in luminance of incident light. In other words, the pixel 302 can detect the event based on a fact that the luminance change has exceeded the predetermined threshold.

Furthermore, as illustrated in FIG. 3, the EVS 200 includes a drive circuit 211, an arbiter unit (arbitration unit) 213, a column processing unit 214, and a signal processing unit 212 as peripheral circuit units of the pixel array unit 300.

When detecting an event, each pixel 302 can output, to the arbiter unit 213, a request for requesting output of event data indicating occurrence of the event. Furthermore, when receiving from the arbiter unit 213 a response indicating permission to output the event data, each pixel 302 outputs the event data to the drive circuit 211 and the signal processing unit 212. Furthermore, the pixel 302 that has detected the event outputs a pixel signal generated by photoelectric conversion to the column processing unit 214.

The drive circuit 211 can drive each pixel 302 of the pixel array unit 300. For example, the drive circuit 211 detects an event, drives the pixel 302 that has output the event data, and outputs a pixel signal of the corresponding pixel 302 to the column processing unit 214.

The arbiter unit 213 arbitrates a request for requesting output of event data supplied from each of the respective pixels 302, and can transmit a response that is based on a result of this arbitration (permission/non-permission of output of the event data), and a reset signal for resetting event detection to the pixel 302.

The column processing unit 214 can perform processing of converting analog pixel signals output from the pixels 302 of a corresponding column into digital signals per column of the pixel array unit 300. The column processing unit 214 can also perform Correlated Double Sampling (CDS) processing on the digitized pixel signal.

The signal processing unit 212 can execute predetermined signal processing on the digitized pixel signals supplied from the column processing unit 214 and the event data output from the pixel array unit 300, and output the event data (time stamp information and the like) and the pixel signal subjected to the signal processing.

The change in the photocurrent generated in the pixel 302 can be regarded as a light quantity change (luminance change) of light incident on the pixel 302. Therefore, the event can also be referred to as a luminance change of the pixel 302 that exceeds the predetermined threshold. Furthermore, event data indicating occurrence of an event can include at least position information such as coordinates indicating the position of the pixel 302 at which the light quantity change that is the event has occurred.

Furthermore, the pixel 302 will be described with reference to FIG. 4. In the pixel array unit 300 configured by aligning the plurality of pixels 302 in a matrix, each pixel 302 includes a light reception unit 304, a pixel signal generation unit 306, and a detection unit (event detection unit) 308.

More specifically, the light reception unit 304 can photoelectrically convert incident light and generate a photocurrent. Furthermore, the light reception unit 304 can supply a signal of a voltage corresponding to the photocurrent to one of the pixel signal generation unit 306 and the detection unit 308 under control of the drive circuit 211.

The pixel signal generation unit 306 can generate a signal supplied from the light reception unit 304 as a pixel signal. Furthermore, the pixel signal generation unit 62 can supply the generated analog pixel signal to the column processing unit 214 via a vertical signal line VSL (not illustrated) corresponding to the column of the pixel array unit 300.

The detection unit 308 can detect whether or not an event has occurred based on whether or not a change amount of the photocurrent from the light reception unit 304 has exceeded a predetermined threshold. The event can include, for example, an on-event that indicates that the change amount of the photocurrent has exceeded an upper limit threshold, and an off-event that indicates that this change amount has fallen below a lower limit threshold. Note that the detection unit 308 may detect only the on-event.

When an event occurs, the detection unit 308 can output to the arbiter unit 213 a request for requesting output of event data indicating the occurrence of the event. Furthermore, when receiving a response to the request from the arbiter unit 213, the detection unit 308 can output the event data to the drive circuit 211 and the signal processing unit 212.

In the embodiments of the present disclosure, by applying this EVS 200 to the endoscopic surgery system 5000, it is possible to make use of a high dynamic range, high robustness for detecting a subject that moves fast, and high time resolution that are the features of the EVS 200, so that it is possible to improve recognition accuracy of the subject.

3. First Embodiment

3.1 Configuration Example of Medical Observation System 10

Figure 5:
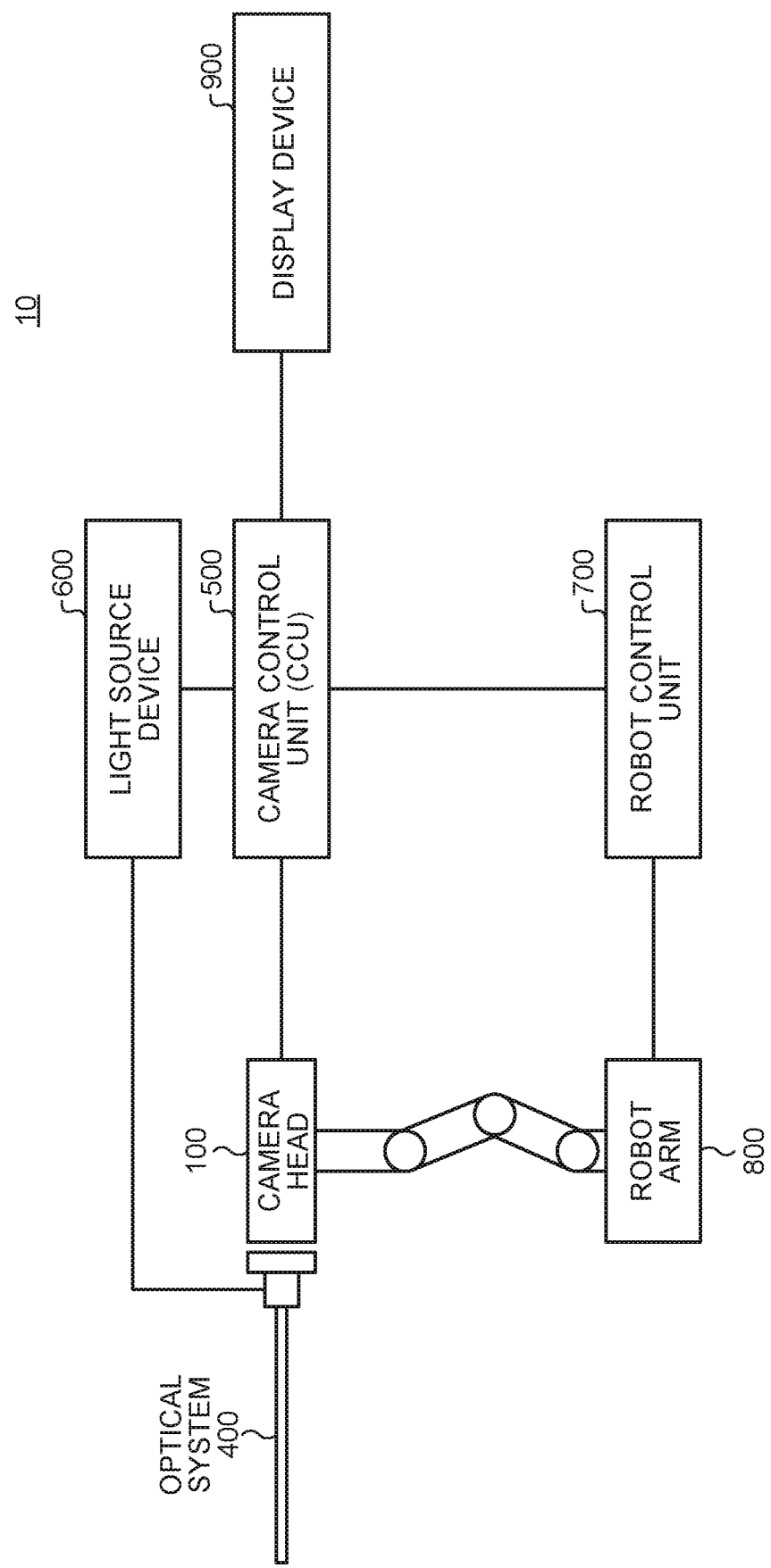
FIG. 5 is a diagram illustrating an example of a configuration of a medical observation system 10 according to a first embodiment of the present disclosure.

First, the configuration example of the medical observation system 10 according to the first embodiment of the present disclosure will be described with reference to FIG. 5. FIG. 5 is a diagram illustrating an example of the configuration of the medical observation system 10 according to the present embodiment. The medical observation system 10 can be applied to an above-described endoscopic surgery system 5000.

As illustrated in FIG. 5, the medical observation system 10 mainly includes a camera head 100 (corresponding to an above-described camera head 5005), an optical system 400 (corresponding to an above-described lens barrel 5003), a Camera Control Unit (CCU) (processing unit) 500 (that tracks an above-described CCU 5039), a light source device 600 (corresponding to an above-described light source device 5043), a robot control unit 700 (corresponding to an above-described arm control device 5045), a robot arm 800 (corresponding to an above-described support arm device 5027), and a display device 900 (corresponding to an above-described display device 5041). Hereinafter, each device included in the medical observation system 10 will be described.

First, an outline of an operation of the medical observation system 10 will be described prior to description of details of the configuration of the medical observation system 10. By controlling the robot arm 800 using the robot control unit 700, the medical observation system 10 can fix positions of the camera head 100 and the optical system 400 supported by the robot arm 800 to suitable positions without someone else's hand. Consequently, the medical observation system 10 can stably obtain an image of a surgical site, so that a surgeon 5067 can smoothly perform surgery. Note that, in the following description, a person who moves or fixes a position of an endoscope 5001 is referred to as a scopist, and an operation of the endoscope 5001 (including movement, stop, change of a posture, zoom-in, zoom-out, and the like) is referred to as scope work regardless of control of someone else's hand or a machine.

(Camera Head 100 and Optical System 400)

The camera head 100 and the optical system 400 are provided at a distal end of the robot arm 800 described later, and image images of various imaging targets (e.g., the environment inside an abdominal cavity). In other words, the robot arm 800 supports the camera head 100 and the optical system 400. Note that the camera head 100 and the optical system 400 may be, for example, an oblique viewing endoscope, a forward viewing endoscope (not illustrated) with a wide angle/cutout function, an endoscope (not illustrated) with a distal end bending function, an endoscope (not illustrated) with an other direction simultaneous photographing function, an exoscope, or a microscope, and are not particularly limited.

Furthermore, the camera head 100 and the optical system 400 can image, for example, a surgical field image including various surgical instruments, organs, and the like in an abdominal cavity of a patient. More specifically, the camera head 100 can function as a camera that can photograph a photographing target in a form of a movie or a still image. Furthermore, the camera head 100 can transmit an electric signal (pixel signal) corresponding to the captured image to the CCU 500 described later. Note that the robot arm 800 may support a surgical instrument such as forceps 5023.

Furthermore, in the embodiments of the present disclosure, the camera head 100 and the optical system 400 may be a stereoscopic endoscope that can perform distance measurement. Alternatively, a depth sensor (distance measurement device) (not illustrated) may be provided in the camera head 100 or separately from the camera head 100. The depth sensor can be, for example, a sensor that performs distance measurement using a Time of Flight (ToF) scheme that performs distance measurement using a return time of reflection of pulsed light from a subject, or a structured light scheme that performs distance measurement based on a distorted pattern by radiating lattice pattern light.

Note that details (more specifically, an RGB sensor and an EVS 200) of the camera head 100 and the optical system 400 according to the present embodiment will be described later.

(CCU 500)

As described above, the CCU 500 includes a CPU, a GPU, and the like, and can integrally control an operation of the camera head 100. More specifically, the CCU 500 can subject a pixel signal accepted from the camera head 100 to various image processing for displaying an image. Furthermore, the CCU 500 provides the pixel signal subjected to the image processing to the display device 900 described later. Furthermore, the CCU 500 can transmit a control signal to the camera head 100 and control driving thereof. The control signal can include information that relates to imaging conditions such as a magnification and a focal distance. Note that details of the CCU 500 according to the present embodiment will be described later.

(Light Source Device 600)

The light source device 600 irradiates an imaging target of the camera head 100 with light. The light source device 600 can be realized by, for example, Light Emitting Diodes (LEDs) for a wide angle lens. For example, the light source device 600 may be configured by combining normal LEDs and a lens, and diffuse light. Furthermore, the light source device 600 may employ a configuration where, for example, a lens diffuses (widen an angle of) light transmitted through an optical fiber (light guide). Furthermore, the light source device 600 may expand an irradiation range by directing optical fibers themselves toward a plurality of directions and radiating light. Note that details of the light source device 600 according to the present embodiment will be described later.

(Robot Control Unit 700)

The robot control unit 700 controls driving of the robot arm 800 described later. The robot control unit 700 is realized by, for example, causing a CPU, an MPU, and the like to execute a program (e.g., a program according to the embodiments of the present disclosure) stored in a storage unit described later using a Random Access Memory (RAM) or the like as a working area. Furthermore, the robot control unit 700 is a controller, and may be realized by, for example, an integrated circuit such as an Application Specific Integrated Circuit (ASIC) or a Field Programmable Gate Array (FPGA). Furthermore, the robot control unit 700 may be a device that is integrated with the above-described CCU 500, or may be a separate device. Note that details of the robot control unit 700 according to the present embodiment will be described later.

(Robot Arm 800)

As described above, the robot arm 800 includes an articulated arm (corresponding to an arm part 5031 illustrated in FIG. 1) that is a multilink structure including a plurality of joint parts and a plurality of links, and can control positions and postures of the camera head 100 and the optical system 400 provided at the distal end of the robot arm 800 by driving the robot arm 800 within a movable range. Furthermore, the robot arm 800 may include a motion sensor (not illustrated) including an acceleration sensor, a gyro sensor, a geomagnetic sensor, and the like to obtain data of the position and posture of the robot arm 800.

(Display Device 900)

The display device 900 displays various images. The display device 900 displays, for example, an image imaged by the camera head 100. The display device 900 can be, for example, a display that includes a Liquid Crystal Display (LCD), an organic Electro-Luminescence (EL) display, or the like. Note that the display device 900 may be the above-described device that is integrated with the CCU 500 illustrated in FIG. 5, or may be the above-described separate device that is connected with the CCU 500 communicably by wire or wirelessly.

3.2 Configuration Example of Camera Head 100 and Optical System 400

Figure 6:
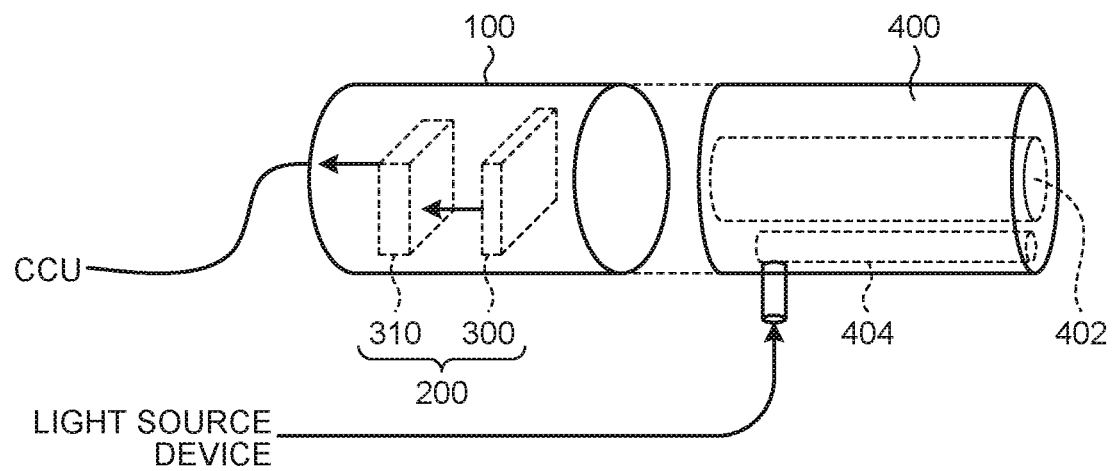
FIG. 6 is an explanatory view for describing an example of a configuration of a camera head 100 and an optical system 400 illustrated in FIG. 5.

Next, an example of a detailed configuration of the camera head (camera head unit) 100 and the optical system 400 according to the present embodiment will be described with reference to FIG. 6. FIG. 6 is an explanatory view for describing an example of the configuration of the camera head 100 and the optical system 400 illustrated in FIG. 5.

(Camera Head 100)

More specifically, as illustrated in FIG. 6, the EVS 200 provided in the camera head 100 includes a substrate on which a pixel array unit 300 is mounted, and a substrate on which a peripheral circuit unit 310 of the pixel array unit 300 is mounted. As described above, the EVS 200 mainly includes a plurality of pixels (first pixels) 302 that are aligned in a matrix, and a detection unit 308 that detects that a luminance change amount of light incident on each of the plurality of pixels 302 has exceeded a predetermined threshold. Furthermore, event data and a pixel signal detected by the EVS 200 are transmitted to the CCU 500. Note that the detailed configuration of the EVS 200 has been described above, and therefore description thereof will be omitted here.

Note that, although the present embodiment has described that the camera head 100 provided with the EVS 200 is different from a camera head provided with an RGB sensor, the EVS 200 and the RGB sensor may be provided in the same camera head as described later. Furthermore, in a case where the camera head 100 provided with the EVS 200 and the camera head provided with the RGB sensor are different, the camera head 100 and the camera head may be supported by the respectively different robot arms 800.

(Optical System 400)

The optical system 400 can guide light from the light source device 600 to a subject, and can guide the light reflected by the subject to the camera head 100. The optical system 400 includes an imaging optical system 402 and a light source optical system 404. More specifically, the light from the light source device 600 is guided to the subject by the light source optical system 404, and the light reflected by the subject is further guided to the camera head 100 by the imaging optical system 402 and condensed on the pixel array unit 300 of the EVS 200. Furthermore, the imaging optical system 402 and the light source optical system 404 are configured by combining a plurality of lenses including zoom lenses and focus lenses. Furthermore, the zoom lenses and the focus lenses may be configured such that positions on optical axes thereof are able to move to, for example, adjust a magnification and a focus of a captured image.

Note that the components such as the camera head 100 and the optical system 400 have sealed structures having high airtightness and waterproofness in the present embodiment, so that the camera head 100 and the optical system 400 can have resistance to autoclave sterilization processing.

Figure 7:
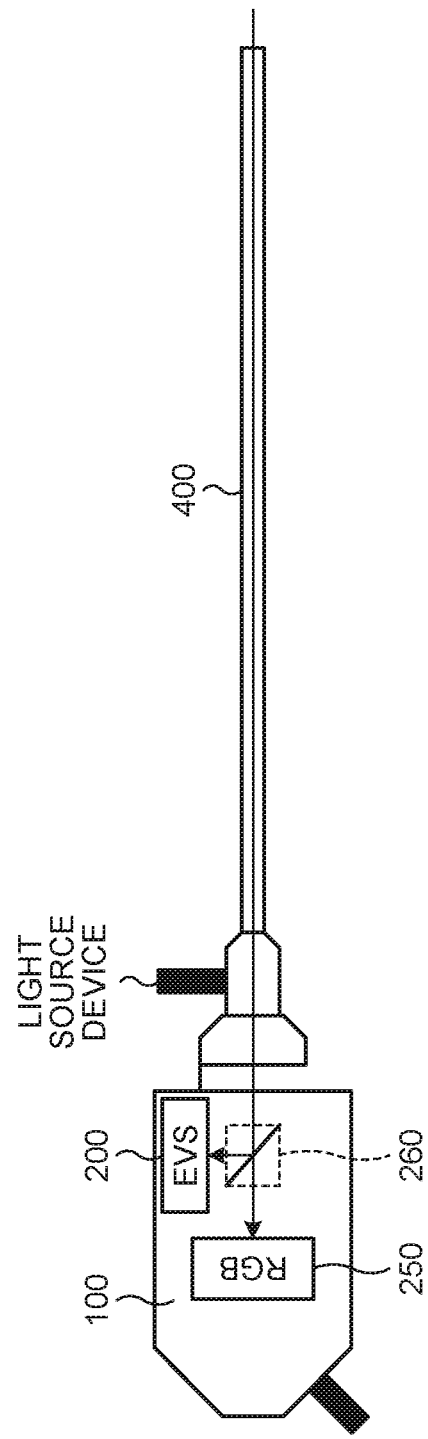
FIG. 7 is an explanatory view for describing another example of the configuration of the camera head 100 according to the first embodiment of the present disclosure.

Furthermore, in the present embodiment, not only the EVS 200 but also an RGB sensor (image detection unit) 250 that images an RGB image may be disposed in the camera head 100. Such a configuration will be described with reference to FIG. 7. FIG. 7 is an explanatory view for describing another example of the configuration of the camera head 100 according to the present embodiment.

The camera head 100 illustrated in FIG. 7 includes the RGB sensor 250 and a prism (dispersion unit) 260 in addition to the EVS 200. More specifically, the RGB sensor 250 provided in the camera head 100 mainly includes a plurality of pixels (second pixels) (not illustrated) that are aligned in a matrix, and a peripheral circuit unit (not illustrated) that outputs as a pixel signal an image that is based on light incident on each of the plurality of pixels 302. Furthermore, the pixel signal output from the RGB sensor 250 is transmitted to the CCU 500. More specifically, the RGB sensor 250 is, for example, an image sensor that has a Bayer arrangement that makes it possible to detect blue light, green light, and red light, and can perform color photographing, and is preferably, for example, an image sensor that can support photographing of a high resolution image of 4K or more. It is possible to obtain an image of a surgical site with high resolution using such an image sensor, so that the surgeon 5067 can grasp a more detailed state of the surgical site and proceed with surgery more smoothly.

Furthermore, the RGB sensor 250 may include a pair of image sensors for respectively acquiring right-eye and left-eye images that support 3D display (stereoscopic system). 3D display is performed, so that the surgeon 5067 can more accurately grasp the depth of living body tissues (organ) at the surgical site, and grasp a distance to the living body tissues.

Furthermore, the prism 260 can guide the light reflected by the subject to both of the EVS 200 and the RGB sensor 250.

Furthermore, the prism (distribution ratio adjustment unit) 260 may have a function of adjusting between the EVS 200 and the RGB sensor 250 a distribution ratio of a light quantity of light incident on each of the EVS 200 and the RGB sensor 250. It is possible to provide the above function by, for example, adjusting a transmittance of the prism 260. More specifically, in a case where, for example, the optical axis of the incident light is the same between the EVS 200 and the RGB sensor 250, it is preferable to adjust the transmittance of the prism 260 such that the light quantity of light incident on the RGB sensor 250 side becomes great.

In the present embodiment, by combining the EVS 200 and the RGB sensor 250, it is possible to make use of both features of a high dynamic range, high robustness for detecting a subject that moves fast, and high time resolution that are features of the EVS 200, and high tracking performance over a long time that is a feature of the RGB sensor 250, so that it is possible to improve recognition accuracy of the subject.

Note that, in the present embodiment, the camera head 100 may include an IR sensor (not illustrated) that detects infrared light.

Note that the present embodiment is not limited to the configuration where the prism 260 guides light to both of the EVS 200 and the RGB sensor 250, and, for example, a hybrid-type sensor may be used in which pixel arrays corresponding to the EVS 200 and the RGB sensor 250 are provided on the same substrate (light reception surface). In such a case, the above-described prism 260 is unnecessary, so that it is possible to simplify rigidity in the camera head 100.

Furthermore, in the embodiments of the present disclosure, the two EVSs 200 and RGB sensors 250 or the three or more EVSs 200 and RGB sensors 250 may be provided to enable the stereoscopic system that can perform distance measurement. Furthermore, in a case where the stereoscopic system is realized, two image circles may be projected on one pixel array by associating the two optical systems 400 with the one pixel array.

Note that, in the present embodiment, the EVS 200 and the RGB sensor 250 may be provided in the distal end part of a flexible endoscope or a rigid endoscope to be inserted in an abdominal cavity.

3.3 Functional Block Configuration Example

Figure 8:
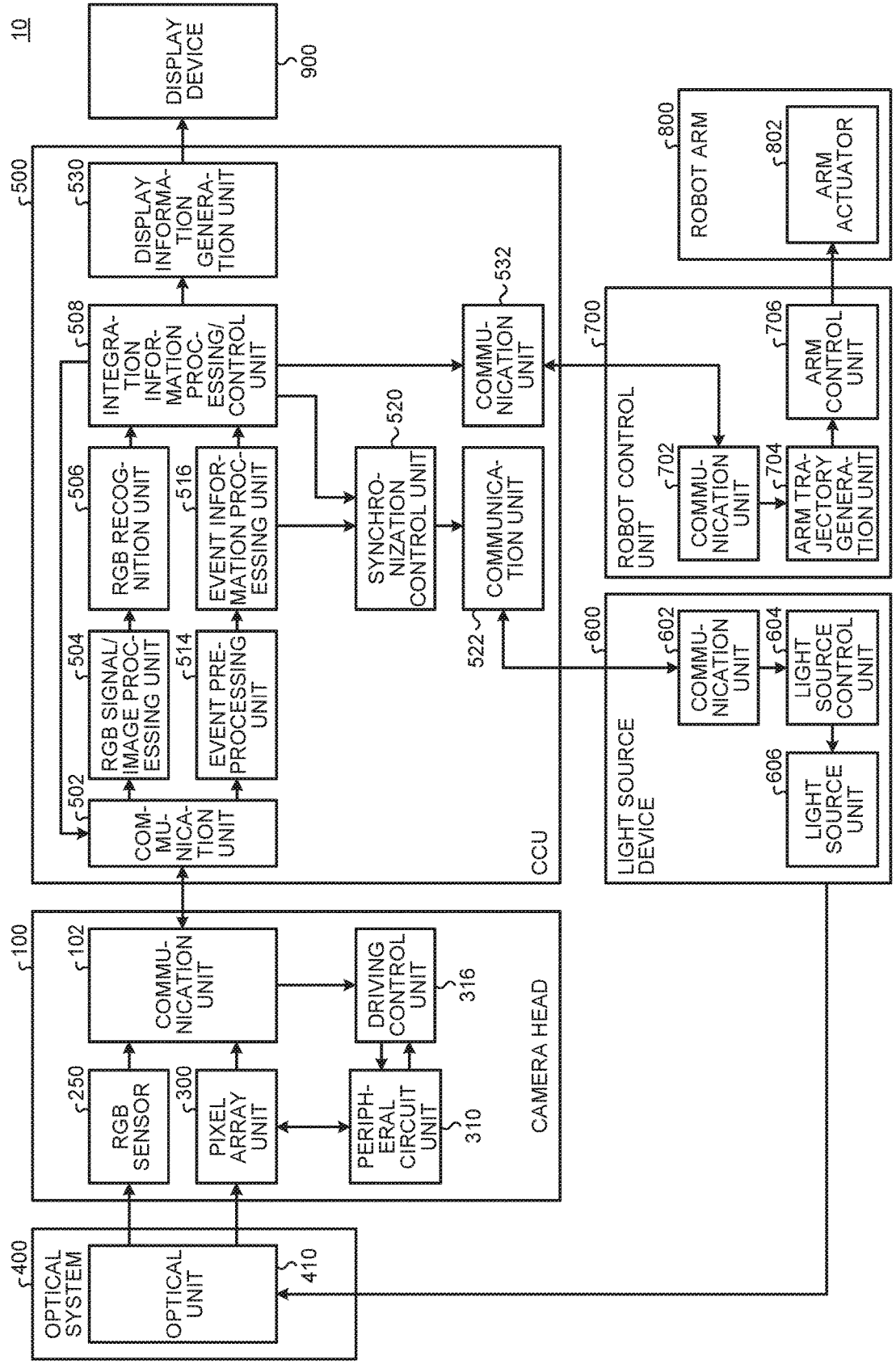
FIG. 8 is a block diagram illustrating an example of a functional block configuration of the medical observation system 10 according to the first embodiment of the present disclosure.

Next, a functional block configuration example of the medical observation system 10 according to the present embodiment will be described with reference to FIG. 8. FIG. 8 is a block diagram illustrating an example of the functional block configuration of the medical observation system 10 according to the present embodiment. As described above, the medical observation system 10 according to the present embodiment mainly includes the camera head 100, the optical system 400, the CCU 500, the light source device 600, the robot control unit 700, the robot arm 800, and the display device 900. Furthermore, the camera head 100, the CCU 500, the light source device 600, and the robot control unit 700 can be bidirectionally communicably connected by a transmission cable (not illustrated).

Alternatively, the camera head 100, the CCU 500, the light source device 600, and the robot control unit 700 may be bidirectionally communicably connected wirelessly. As described above, in a case where communication is performed wirelessly, it is not necessary to lay the transmission cable in an operating room, so that it is possible to overcome a situation that movement of a medical staff (e.g., surgeon 5067) in the operating room is hindered by the transmission cable. Hereinafter, each device included in the medical observation system 10 will be described.

(Camera Head 100)

As illustrated in FIG. 8, the camera head 100 mainly includes the pixel array unit 300 and the peripheral circuit unit 310 of the EVS (imaging unit) 200, the RGB sensor 250, a communication unit 102, and a drive control unit 316. More specifically, the pixel array unit 300 and the RGB sensor 250 of the EVS 200 receive light guided by an optical unit 410 including a plurality of lenses, generate a signal, and output the generated signal to the communication unit 102.

The communication unit 102 includes a communication device for transmitting and receiving various pieces of information to and from the CCU 500, and can transmit signals from the pixel array unit 300 and the RGB sensor 250 to the CCU 500, and receive from the CCU 500 a control signal for controlling driving of the camera head 100. The control signal includes, for example, information related to imaging conditions such as information for designating a frame rate of imaging, information for designating an exposure value at a time of imaging, and/or information for designating a magnification and a focus of a captured image. Note that the imaging conditions such as the above frame rate, exposure value, magnification, and focus may be automatically set by an integration information processing/control unit 508 of the CCU 500 based on the acquired image or the like.

The drive control unit 316 controls driving of the EVS 200 based on the control signal received from the CCU 500 via the communication unit 102. For example, the drive control unit 316 adjusts a threshold or the like to be compared with the luminance change amount when detecting an event.

(CCU 500)

As illustrated in FIG. 8, the CCU 500 mainly includes communication units 502, 522, and 532, an RGB signal/image processing unit 504, an RGB recognition unit 506, the integration information processing/control unit 508, an event preprocessing unit 514, an event information processing unit 516, a synchronization control unit 520, and a display information generation unit 530.

The communication units 502, 522, and 532 include communication devices for transmitting and receiving various pieces of information (detection signals, control signals, and the like) to and from each of the camera head 100, the light source device 600, and the robot control unit 700. In the present embodiment, by providing these communication units 502, 522, and 532, it is possible to enable cooperation between the camera head 100, the light source device 600, and the robot arm 800.

The RGB signal/image processing unit 504 can perform various image processing on a pixel signal that is RAW data acquired via the communication unit 502 and transmitted from the RGB sensor 250 of the camera head 100, and output the pixel signal to the RGB recognition unit 506 described later. The image processing includes, for example, various known signal processing such as development processing, image quality improvement processing (band enhancement processing, super-resolution processing, Noise Reduction (NR) processing, camera shake correction processing, and/or the like), and/or enlargement processing (electronic zoom processing). More specifically, the RGB signal/image processing unit 504 includes a processor such as a CPU and a GPU, and the processor operates according to a predetermined program to perform the above-described image processing. Note that, in a case where the RGB signal/image processing unit 504 includes a plurality of GPUs, the RGB signal/image processing unit 504 may appropriately divide information related to the pixel signal, and the plurality of these GPUs may perform image processing on the information in parallel.

The RGB recognition unit 506 can perform recognition processing on the image processed by the RGB signal/image processing unit 504 to obtain information for controlling the RGB sensor 250, the light source device 600, and the robot arm 800. For example, the RGB recognition unit 506 can recognize a position, a shape, sharpness, a luminance, and the like of the subject from the image, and obtain information for controlling focus of the RGB sensor 250, an intensity and a range of light radiated from the light source device 600, driving of the robot arm 800, and the like. The obtained information is output to the integration information processing/control unit 508 described later. Furthermore, the RGB recognition unit 506 can recognize a surgical instrument such as forceps, a specific living body site, bleeding, and the like by segmenting a subject included in each surgical site image using various image recognition techniques.

The integration information processing/control unit (processing unit) 508 performs various processing related to control of the EVS 200 and the RGB sensor 250, and image display that uses various pixel signals (first and second outputs) from the EVS 200 and the RGB sensor 250. For example, the integration information processing/control unit 508 generates a control signal for controlling the EVS 200 and the RGB sensor 250. At this time, in a case where imaging conditions are input by the surgeon 5067, the integration information processing/control unit 508 may generate a control signal based on the input of the surgeon 5067. Furthermore, the integration information processing/ control unit 508 can integrate signals from the EVS 200 and the RGB sensor 250, or arbitrate images from the EVS 200 and the RGB sensor 250 having different frame rates, and simultaneously handle the images.

Furthermore, the integration information processing/control unit 508 may perform processing such as image quality enhancement, three-dimensional shape measurement, optical flow estimation (for, for example, estimating an apparent speed of an object in an image, or estimating and tracking a moving object from the image), visual inertial odometry (for estimating and tracking a posture of a camera by combining an image with motion data), motion detection, segmentation, image recognition, and Simultaneous Localization And Mapping (SLAM).

Thus, in the present embodiment, the integration information processing/control unit 508 can perform integration processing on output information from the EVS 200 and the RGB sensor 250, so that it is possible to clearly capture an edge of the subject even in a dark area based on, for example, the output from the EVS 200. Furthermore, the EVS 200 has high time resolution, and can consequently compensate for tracking of a subject of a low frame rate performed by the RGB sensor 250, so that it is possible to improve tracking performance for a subject that moves at a high speed or deforms in the present embodiment. Furthermore, the output information of the EVS 200 is sparse information, so that it is possible to reduce a processing load according to the present embodiment.

Note that, in the present embodiment, the integration information processing/control unit 508 is not limited to performing the integration processing on the output information from the EVS 200 and the RGB sensor 250, and may individually process the output information.

The event preprocessing unit 514 can perform various processing on the event data and the pixel signal that are RAW data acquired via the communication unit 502 and transmitted from the EVS 200 of the camera head 100, and output the event data and the pixel signal to the event information processing unit 516 described later. The processing includes, for example, integration of pixel signals of a certain period (frame length) from the EVS 200, and adjustment of the frame length. More specifically, the event preprocessing unit 514 includes processors such as a CPU and a GPU, and the processors operate according to a predetermined program to perform the above-described processing.

The event information processing unit 516 can perform image processing based on the event data and the pixel signal processed by the event preprocessing unit 514. Furthermore, by detecting a shape of the edge of the subject included in each surgical site image using various image recognition techniques, the event information processing unit 516 may recognize a surgical instrument such as forceps, a specific living body site, a shape, bleeding, or the like.

The synchronization control unit 520 generates a synchronization control signal for synchronizing the camera head 100 and the light source device 600 based on the control signal of the integration information processing/control unit 508, and controls the light source device 600 via the communication unit 522. For example, by adjusting an intensity and a cycle of an intensity change of the light radiated from the light source device 600 based on the information of brightness of a screen that is based on the image from the RGB sensor 250, the EVS 200 can more suitably perform imaging.

The display information generation unit 530 causes the display device 900 to display the image of the surgical site based on the pixel signal processed by the integration information processing/control unit 508. In the present embodiment, the display information generation unit 530 may cause the display device 900 to display not only the image of the surgical site, but also segmentation information that follows, for example, a size, a distance, deformation, and the like of an organ.

(Light Source Device 600)

As illustrated in FIG. 8, the light source device 600 mainly includes a communication unit 602, a light source control unit 604, and a light source unit 606. The communication unit 602 includes a communication device for transmitting and receiving various pieces of information (a control signal and the like) to and from the CCU 500. The light source control unit 604 controls driving of the light source unit 606 based on the control signal received from the CCU 500 via the communication unit 602. The light source unit 606 includes a light source such as an LED, and supplies irradiation light to a surgical site under control of the light source control unit 604.

(Robot Control Unit 700)

As illustrated in FIG. 8, the robot control unit (control unit) 700 mainly includes a communication unit 702, an arm trajectory generation unit 704, and an arm control unit 706. The communication unit 702 includes a communication device for transmitting and receiving various pieces of information (a control signal and the like) to and from the CCU 500. The arm trajectory generation unit 704 can generate trajectory information as autonomous operation control information for causing the robot arm 800 to autonomously operate based on the control information from the CCU 500. Furthermore, the arm control unit 706 controls driving of an arm actuator 802 of the robot arm 800 based on the generated trajectory information. In the present embodiment, a sudden motion of the surgical instrument that is the subject can also be detected in real time by the EVS 200 having high time resolution, so that the robot arm 800 can more instantaneously move the camera head 100 without interfering with the surgical instrument. Consequently, it is possible to safely perform surgery.

3.4 Control Method

Figure 9:
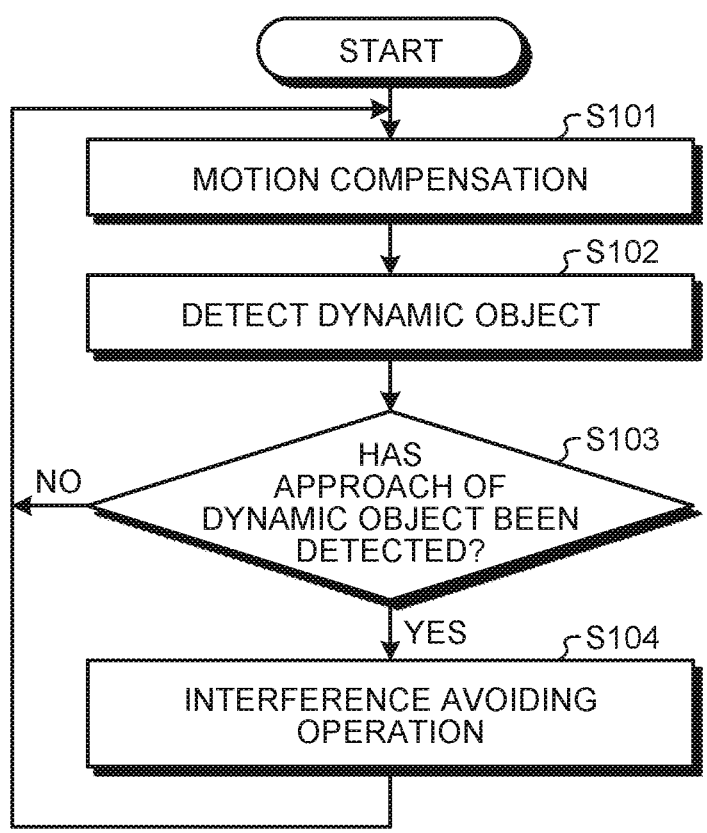
FIG. 9 is a flowchart of a control method according to the first embodiment of the present disclosure.
Figure 10:
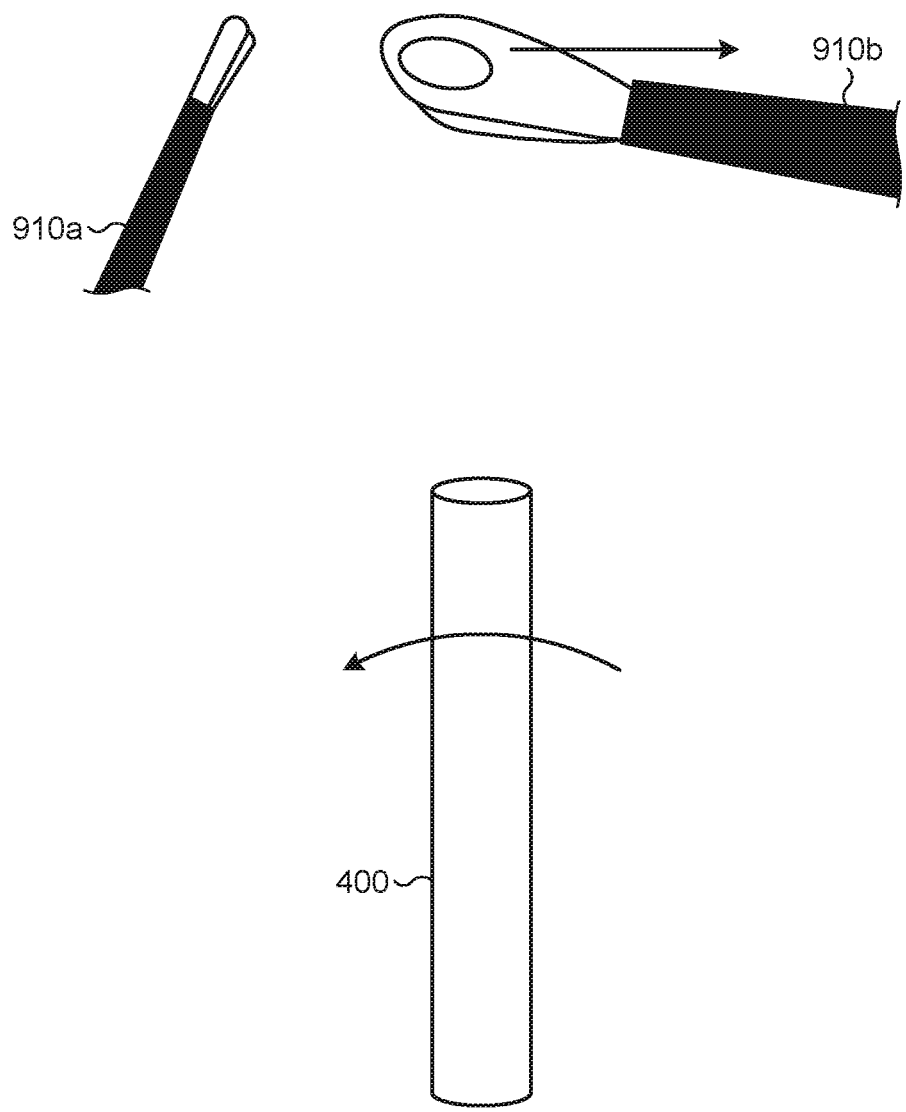
FIG. 10 is an explanatory view for describing the control method according to the first embodiment of the present disclosure.
Figure 11:
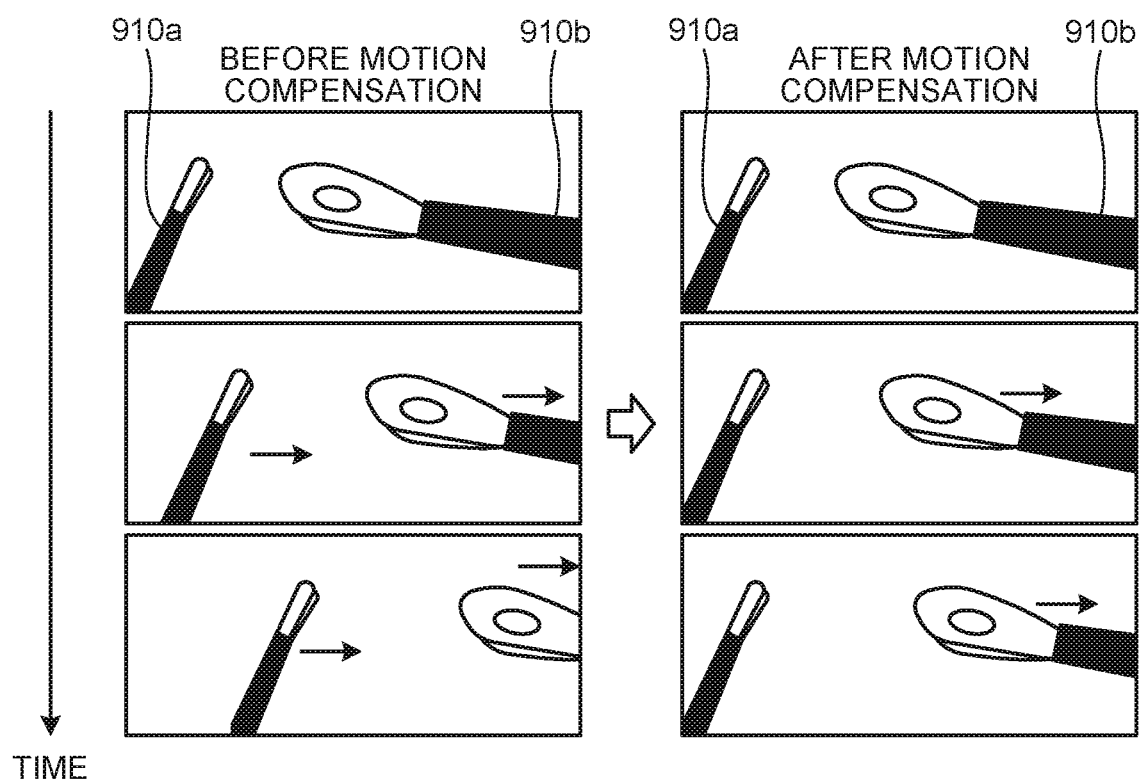
FIG. 11 is an explanatory view for describing motion compensation of the control method according to the first embodiment of the present disclosure.

Next, an example of the control method according to the first embodiment of the present disclosure will be described with reference to FIGS. 9 to 11. FIG. 9 is a flowchart of the control method according to the present embodiment. FIG. 10 is an explanatory view for describing the control method according to the present embodiment, and FIG. 11 is an explanatory view for describing motion compensation of the control method according to the present embodiment.

By the way, during laparoscopic surgery, an erroneous operation of the surgical instrument or the like causes a surgical instrument and an endoscope (the camera head 100 and the optical system 400) to contact. As a result, dirt adheres to the endoscope, and labor is required to take out the endoscope to an outside of the body and clean the endoscope, which is a cause that an operation time becomes long.

For this reason, it is required to avoid contact (interference) with the surgical instrument using the robot arm 800 that supports the endoscope (the camera head 100 and the optical system 400). However, the RGB sensor 250 used for the conventional techniques takes several 10 to 100 ms to perform image recognition on the surgical instrument, and then an avoidance operation of the robot arm 800 is started. Therefore, according to the autonomous operation of the robot arm 800 based on the image recognition that uses the RGB sensor 250, it has not been possible to adapt to a sudden motion of the surgical instrument and a quick motion such as drop of a raised organ.

On the other hand, in the present embodiment, by using image recognition of the EVS 200, the robot arm 800 can avoid the sudden motion of the surgical instrument and the quick motion such as drop of the raised organ.

More specifically, as illustrated in FIG. 9, the control method according to the present embodiment can mainly include steps of step S101 to step S104. Details of these respective steps according to the present embodiment will be described below.

Hereinafter, a case where the optical system 400 and the camera head 100 moved by the robot arm 800 image a surgical instrument 910*a* that does not move and a surgical instrument 910*b* that moves as illustrated in FIG. 10 will be described as an example.

First, the medical observation system 10 executes motion compensation processing of canceling motions of the optical system 400 and the camera head 100 using an image captured at a high frame rate by the EVS 200 (step S101). More specifically, for example, the medical observation system 10 detects a motion vector from an entire image (in an example on the left side of FIG. 11, the optical system 400 and the camera head 100 are moving, and therefore that the surgical instruments 910*a* and 910*b* are moving is captured) before the motion compensation processing illustrated on the left side of FIG. 11, and corrects the image using the detected motion vector, so that it is possible to obtain an image (in the example on the right side of FIG. 11, the motions of the optical system 400 and the camera head 100 are canceled, and therefore the surgical instrument 910*a* stops and the surgical instrument 910*b* is moving) after motion compensation illustrated on the right side of FIG. 11. Furthermore, at this time, the image may be corrected using position/motion information of the camera/endoscope obtained from the robot in addition to the motion vector to obtain the image after motion compensation.

Next, the medical observation system 10 detects a dynamic object (here, the moving surgical instrument 910*b*) that is making a motion, from the image after motion compensation obtained in step S101 (step S102).

Next, by, for example, making use of time series data of the images or using stereoscopic distance measurement, or the like for the dynamic object (here, the moving surgical instrument 910*b*) detected in step S102, the medical observation system 10 detects the distance to the dynamic object. Furthermore, the medical observation system 10 determines whether or not the dynamic object approaches the camera head 100 and the optical system 400 based on the detected distance (step S103). The medical observation system 10 proceeds to step S104 in a case where the dynamic object approaches (step S103: Yes), and returns to above-described step S101 in a case where the dynamic object does not approach (step S103: No).

Furthermore, the medical observation system 10 causes the robot arm 800 to autonomously operate to avoid interference and collision with the dynamic object (here, the moving surgical instrument 910*b*) using the distance detected in step S103 or the like (step S104).

As described above, the present embodiment provides high robustness for detecting a subject that moves fast, and high time resolution that are features of the EVS 200, so that it is possible to quickly capture the surgical instrument by performing image recognition on an EVS image of the EVS 200. Furthermore, in the present embodiment, such image recognition enables the robot arm 800 to avoid a sudden motion of the surgical instrument and a quick motion such as drop of a raised organ. That is, according to the present embodiment, it is possible to robustly and highly accurately measure and recognize an environment inside an abdominal cavity in real time, so that it is also possible to make scope work of the endoscopic surgery system 5000 autonomous.

3.5 Modified Example

First Modified Example

Figure 12:
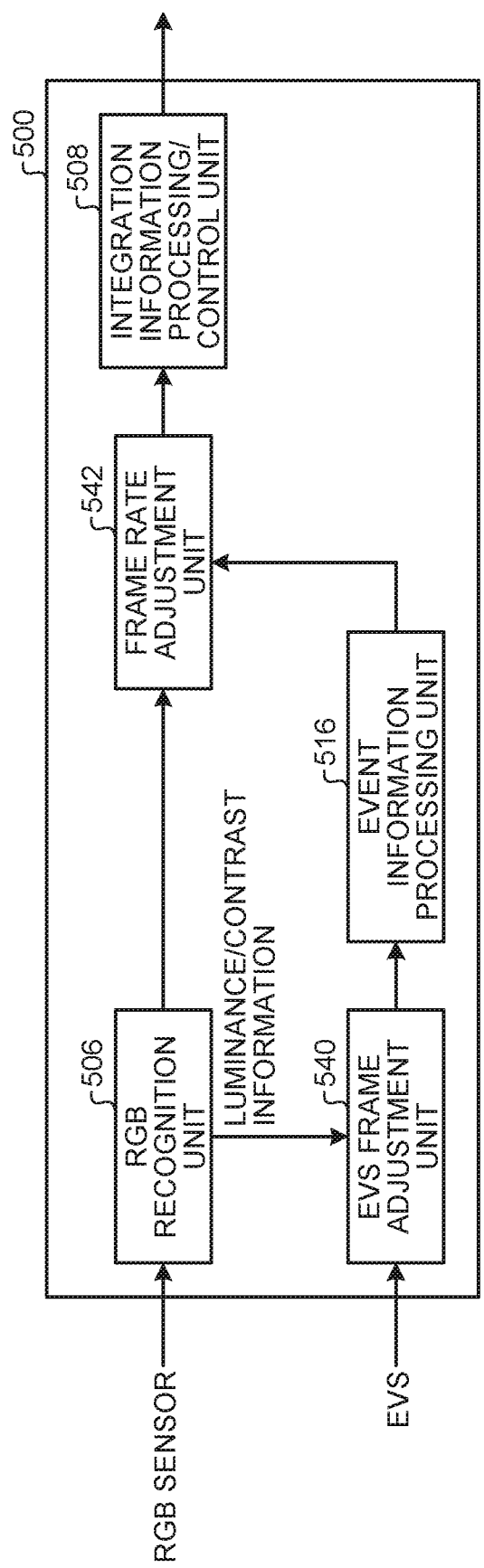
FIG. 12 is a functional block diagram illustrating main components of a CCU 500 according to a first modified example according to the first embodiment of the present disclosure.

Furthermore, in the first modified example of the present embodiment, frame rates of the EVS 200 and the RGB sensor 250 having different frame rates may be adjusted to improve accuracy of image recognition. Such a modified example will be described with reference to FIG. 12. FIG. 12 is a functional block diagram illustrating main components of the CCU 500 according to the first modified example of the present embodiment.

As illustrated in FIG. 12, the CCU 500 according to the first modified example may include a frame rate adjustment unit 542 provided between the above-described RGB recognition unit 506 and integration information processing/control unit 508, and an EVS frame adjustment unit 540 provided between the event preprocessing unit 514 (not illustrated in FIG. 12) and the event information processing unit 516.

More specifically, the RGB recognition unit 506 acquires an image at a low frame rate of, for example, approximately 30 fps using the RGB sensor 250, acquires luminance and contrast information from the image, and outputs the acquired information to the EVS frame adjustment unit 540.

Next, based on the acquired information, the EVS frame adjustment unit (adjustment unit) 540 determines a frame length that is a period for integrating the pixel signals from the EVS 200, and a frequency for thinning out the pixel signals (images) from the EVS 200. Note that the frame length or the like may be determined using a model obtained by machine learning in the present modified example. By so doing, it is possible to further improve recognition accuracy of a shape (edge information) of the subject of interest from the EVS image of the EVS 200.

Furthermore, the event information processing unit 516 generates a suitable EVS image by integrating or performing thinning processing on pixel signals from the EVS 200 based on the determination of the EVS frame adjustment unit 540. Furthermore, the event information processing unit 516 may perform subject recognition or the like based on the shape (edge information) of the subject in the generated EVS image.

Furthermore, the frame rate adjustment unit 542 adjusts a frame rate of the image or the like such that that the integration information processing/control unit 508 can suitably perform the integration processing on the EVS image from which the edge information of the subject can be obtained, and the RGB image that is obtained from the RGB sensor 250 and from which segment information of the subject can be obtained. Furthermore, the integration information processing/control unit 508 can accurately recognize the subject by performing integration processing on the adjusted EVS image from which the edge information of the subject can be obtained, and RGB image from which the segment information of the subject can be obtained. Consequently, according to the present modified example, it is possible to robustly and accurately recognize a tumor or the like that is a surgical site even in, for example, a dark abdominal cavity.

Second Modified Example

Furthermore, in the second modified example of the present embodiment, an angle of view indicating a range of a scene captured by the EVS 200 and an angle of view indicating a range of a scene captured by the RGB sensor 250 may be different. In a case where, for example, an image (e.g., an image of the entire inside of the abdominal cavity) for controlling the operation of the robot arm 800 is captured by the EVS 200, the angle of view indicating the range of the scene captured by the EVS 200 may be made wider than the angle of view indicating the range of the scene captured by the RGB sensor 250 that captures the image (e.g., the image of the tumor that is the surgical site) required by a doctor who does surgery. That is, in present second modified example, the angles of view of the EVS 200 and the RGB sensor 250 may be suitably set according to a use method.

4. Second Embodiment

By the way, an EVS 200 cannot detect an event unless a luminance changes a predetermined threshold or more. Therefore, the EVS 200 cannot capture a subject whose luminance does not change or changes little. Hence, in the second embodiment of the present disclosure, by providing a drive unit that forcibly moves the EVS 200 in a predetermined direction, and thereby forcibly causing luminance to change, the EVS 200 may be encouraged to detect an event.

Figure 13:
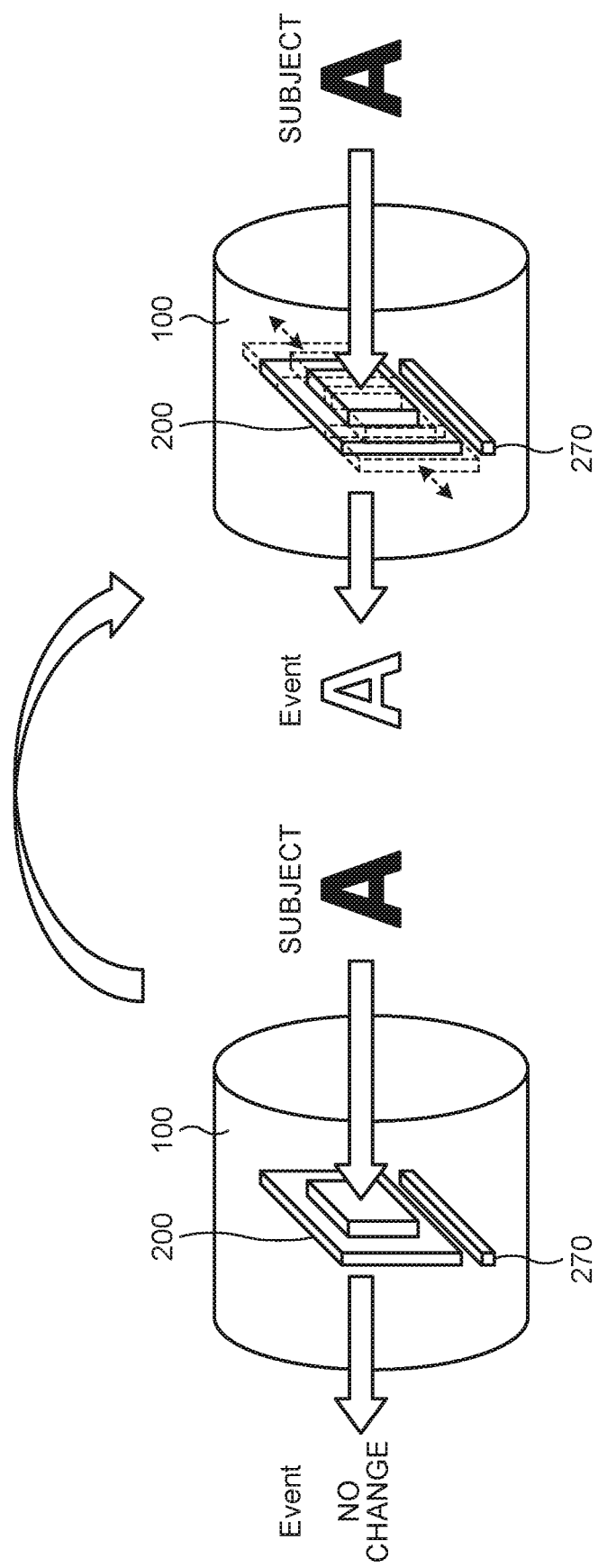
FIG. 13 is an explanatory view for describing an example of a configuration of a camera head 100 according to a second embodiment of the present disclosure.

The second embodiment where an actuator (drive unit) 270 that moves the EVS 200 itself along the predetermined direction is provided will be described with reference to FIG. 13. FIG. 13 is an explanatory view for describing an example of a configuration of a camera head 100 according to the present embodiment.

As illustrated on the left side of FIG. 13, when a subject does not make a motion, luminance does not change, an event does not occur, and therefore the EVS 200 cannot capture an image of the subject. Therefore, in the present embodiment, to cause the EVS 200 to forcibly capture the image of the subject, the actuator 270 that can finely move the EVS 200 in a left-right direction is provided as illustrated on the right side of FIG. 13. In the present embodiment, by causing the actuator 270 to finely move the EVS 200 itself, the EVS 200 detects a luminance change, so that it is possible to capture an image of the subject that does not move. Note that the present embodiment is not limited to the actuator 270 that moves the EVS 200 in the left-right direction, and may be the actuator 270 that finely moves the EVS 200 in an upward-downward direction. Furthermore, the present embodiment is not limited to the actuator that moves the EVS 200, and an actuator that drives an optical system 400 may be provided.

Furthermore, in the present embodiment, when the EVS 200 cannot detect the subject, the EVS 200 and a light source device 600 may cooperate to change the intensity of light in a short period (i.e., may change a light irradiation cycle) such that a luminance change becomes great. Furthermore, in the present embodiment, when the EVS 200 cannot detect the subject, a threshold to be compared with a luminance change amount may be dynamically changed.

As described above, according to the present embodiment, the EVS 200 can capture even a subject whose luminance does not change or changes little.

5. Third Embodiment

Figure 14:
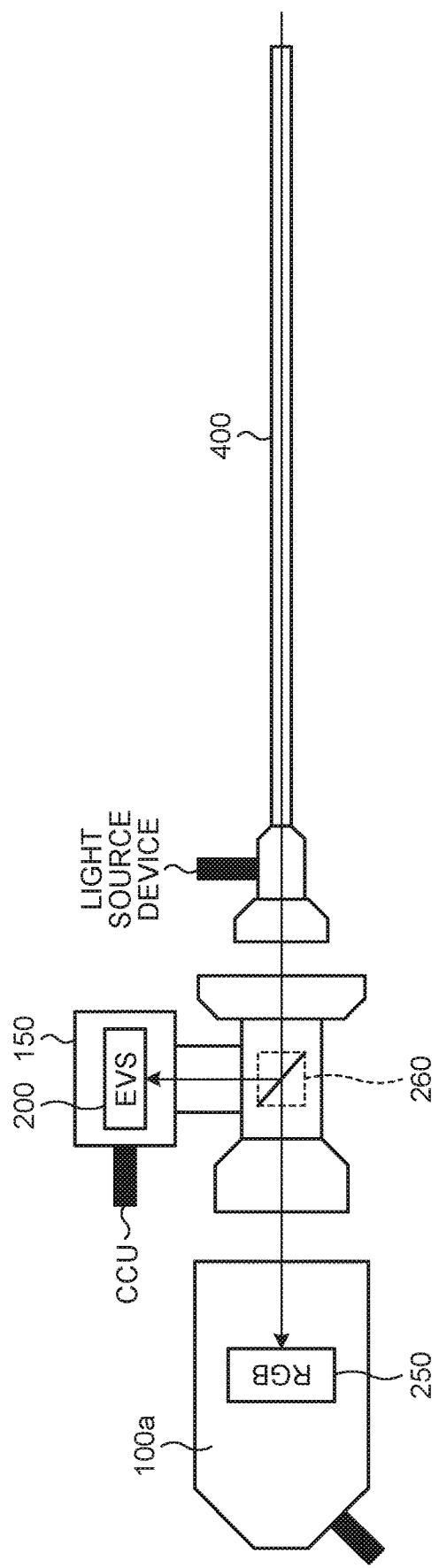
FIG. 14 is an explanatory view for describing an example of a configuration of an adapter 150 according to a third embodiment of the present disclosure.

Furthermore, in the third embodiment of the present disclosure described below, an adapter may be attached between a conventional camera head 100*a* and an optical system 400 to enable use of an EVS 200. This third embodiment of the present disclosure will be described with reference to FIG. 14. FIG. 14 is an explanatory view for describing an example of a configuration of an adapter 150 according to the present embodiment.

More specifically, as illustrated in FIG. 14, the adapter 150 according to the present embodiment can be attached (inserted) between the conventional camera head 100*a* including only an RGB sensor 250, and the optical system 400. The adapter 150 includes a prism 260 that disperses light guided from the optical system 400, to the RGB sensor 250 of the camera head 100*a* and the EVS 200 in the adapter 150, and the EVS 200.

Furthermore, in the present embodiment, pixel signals from the EVS 200 and the like can be transmitted to a CCU 500 connected with the RGB sensor 250, and pixel signals or images of two sensors may be subjected to integration processing in the CCU 500. Alternatively, in the present embodiment, the EVS 200 and the RGB sensor 250 may be connected to separate CCUs, and the pixel signals from these sensors and the like may be processed separately, or may be processed separately, and then be subjected to the integration processing by another information processing device.

As described above, by using the adapter 150 according to the present embodiment, it is possible to easily extend functions such that even an endoscope including the conventional camera head 100*a* including only the RGB sensor 250 can use a function of the EVS 200.

6. Fourth Embodiment 6.1 First Example

By the way, as described above, to avoid a camera head 100 and an optical system 400 supported by a robot arm 800 and a surgical instrument from damaging other organs and tissues when a tumor is excised, the endoscopic surgery system 5000 is required to highly accurately recognize a tumor position at a high speed, and cause the robot arm 800 to autonomously operate according to a recognition result. However, image recognition that uses an RGB image of a conventional RGB sensor has a limit in increasing a frame rate. When a tumor moves at a high speed due to pulsation or the like, a tumor position is tracked while predicting a motion of the tumor using RGB images of previous and subsequent frames. In such a case, a time between frames is long, therefore it is not possible to accurately predict the motion of the tumor that moves at a high speed, the tumor deviates from a set Region Of Interest (ROI), and it is not possible to track the tumor.

Furthermore, although it is also conceivable to set a wide ROI such that the tumor always enters the ROI at a time of tracking, if the ROI is widened, a processing time becomes long. Furthermore, although it is conceivable to attach a high speed camera as alternative means, an inside of an abdominal cavity is narrow, includes many shields, and is dark, and therefore the high speed camera interferes with other sensors, or it is difficult for the high speed camera to clearly capture a subject.

Figure 15:
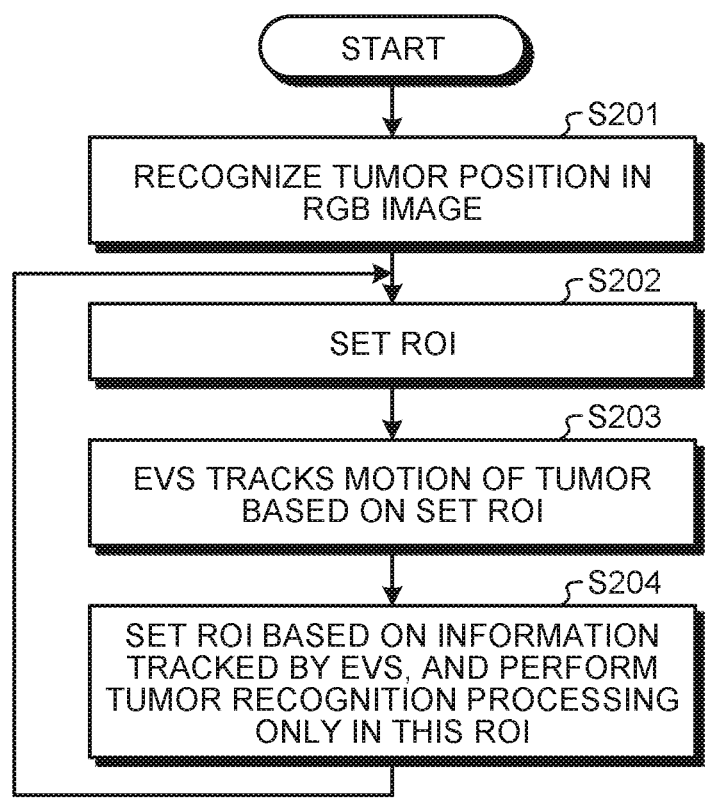
FIG. 15 is a flowchart of an image recognition method according to a first example of a fourth embodiment of the present disclosure.

Therefore, in the fourth embodiment of the present disclosure, an RGB sensor 250 and an EVS 200 are combined to make an EVS sensor highly accurately track the tumor position at a high speed, set an ROI on an RGB image based on tracked information, and perform image recognition on the subject. In the present embodiment, high robustness for detecting a subject that moves fast and high time resolution that are features of the EVS 200 make it possible to highly accurately track the tumor position at a high speed. Hereinafter, the present embodiment will be described with reference to FIGS. 15 and 16. FIG. 15 is a flowchart of an image recognition method according to the first example of the present embodiment, and FIG. 16 is an explanatory view for describing the first example of the present embodiment.

As illustrated in FIG. 15, the image recognition method according to the present example can mainly include steps of step S201 to step S204. Details of these respective steps according to the present example will be described below.

Figure 16:
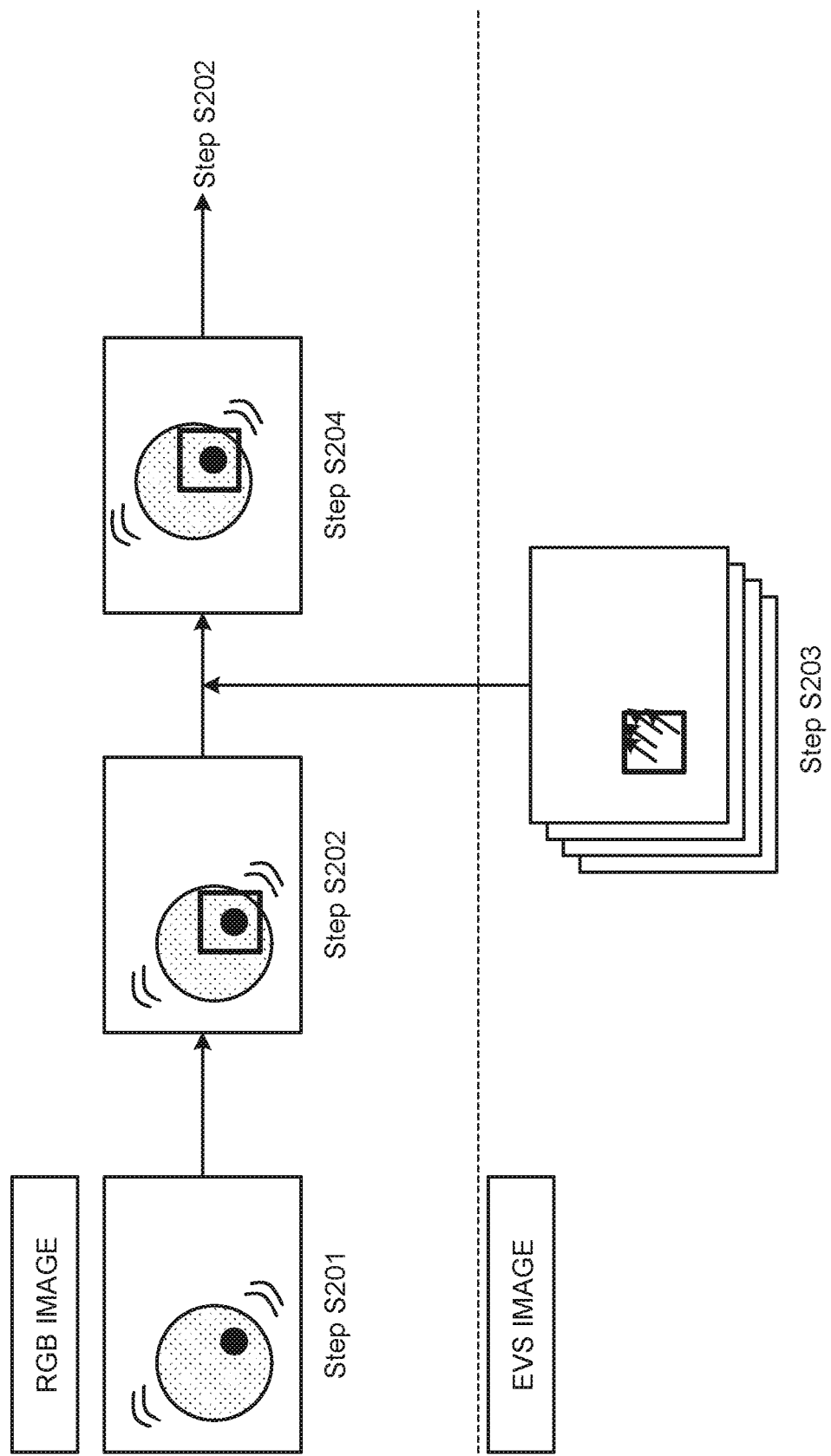
FIG. 16 is an explanatory view for describing the first example of the fourth embodiment of the present disclosure.

More specifically, as illustrated in an upper part of FIG. 16, a medical observation system 10 first recognizes the tumor position using an RGB image of the RGB sensor 250 (step S201). Furthermore, as illustrated in the upper part of FIG. 16, the medical observation system 10 sets an ROI (illustrated by a bold frame in FIG. 16) based on the recognized tumor position (step S202).

Next, as illustrated in the lower part of FIG. 16, the medical observation system 10 tracks the tumor that moves at a high speed using the EVS 200 based on the set ROI (step S203). Note that, although it is required to narrow the ROI as much as possible when tracking is performed using the RGB image, the EVS 200 operates upon detection of an event in response to a luminance change, so that it is not essential to set the narrow ROI, and it is possible to control accuracy of tracking by setting a threshold to be compared with the luminance change. For example, the threshold may be locally lowered, and detection sensitivity may be increased in the first example.

Furthermore, as illustrated in the upper part of FIG. 16, the medical observation system 10 sets the ROI on the RGB image based on a tracking result of the EVS 200, and performs image recognition processing on the tumor using an image in the set ROI (step S204). In the first example, the EVS 200 performs highly accurate tracking, so that it possible to narrow the ROI set on the RGB image. Consequently, according to the first example, it is possible to reduce a load of the image recognition processing of the tumor in the RGB image.

6.2 Second Example

Figure 17:
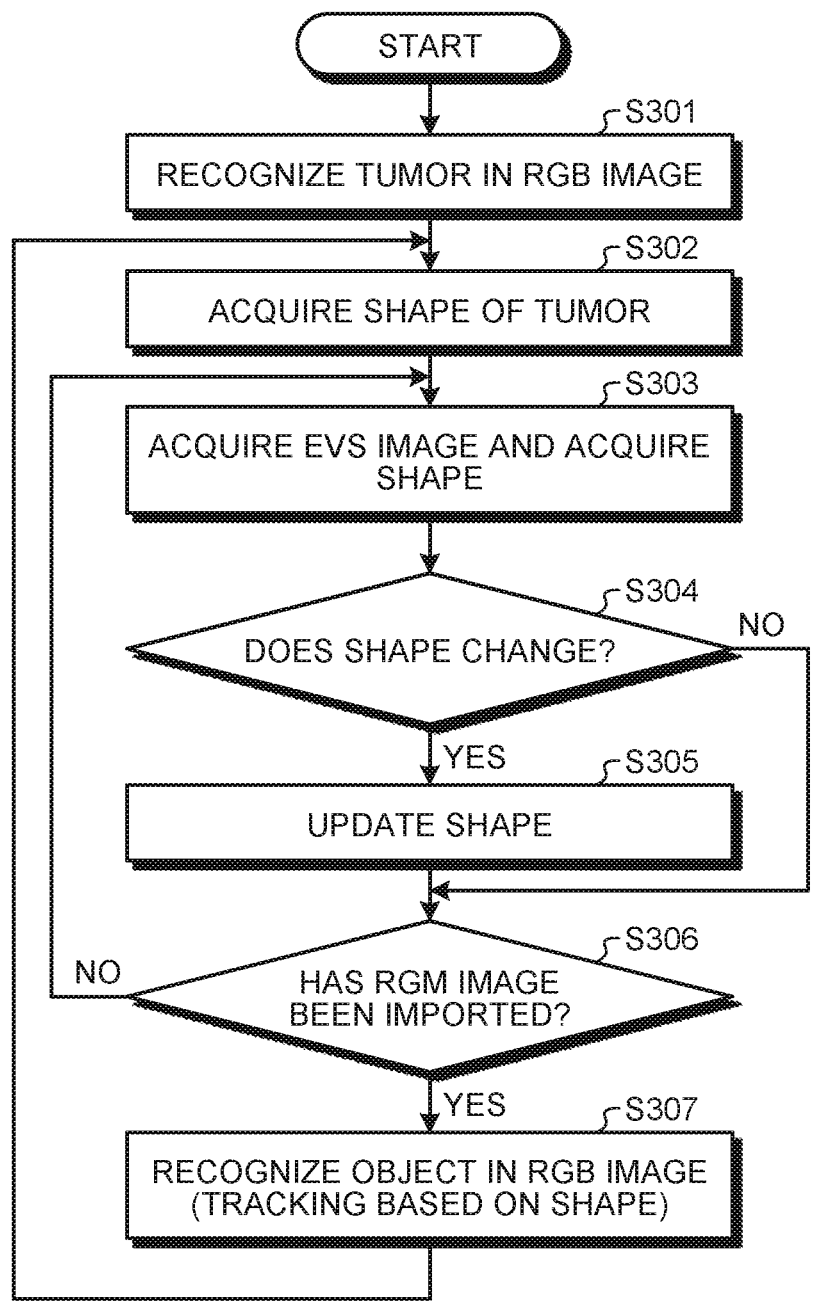
FIG. 17 is a flowchart of an image recognition method according to a second example of the fourth embodiment of the present disclosure.
Figure 18:
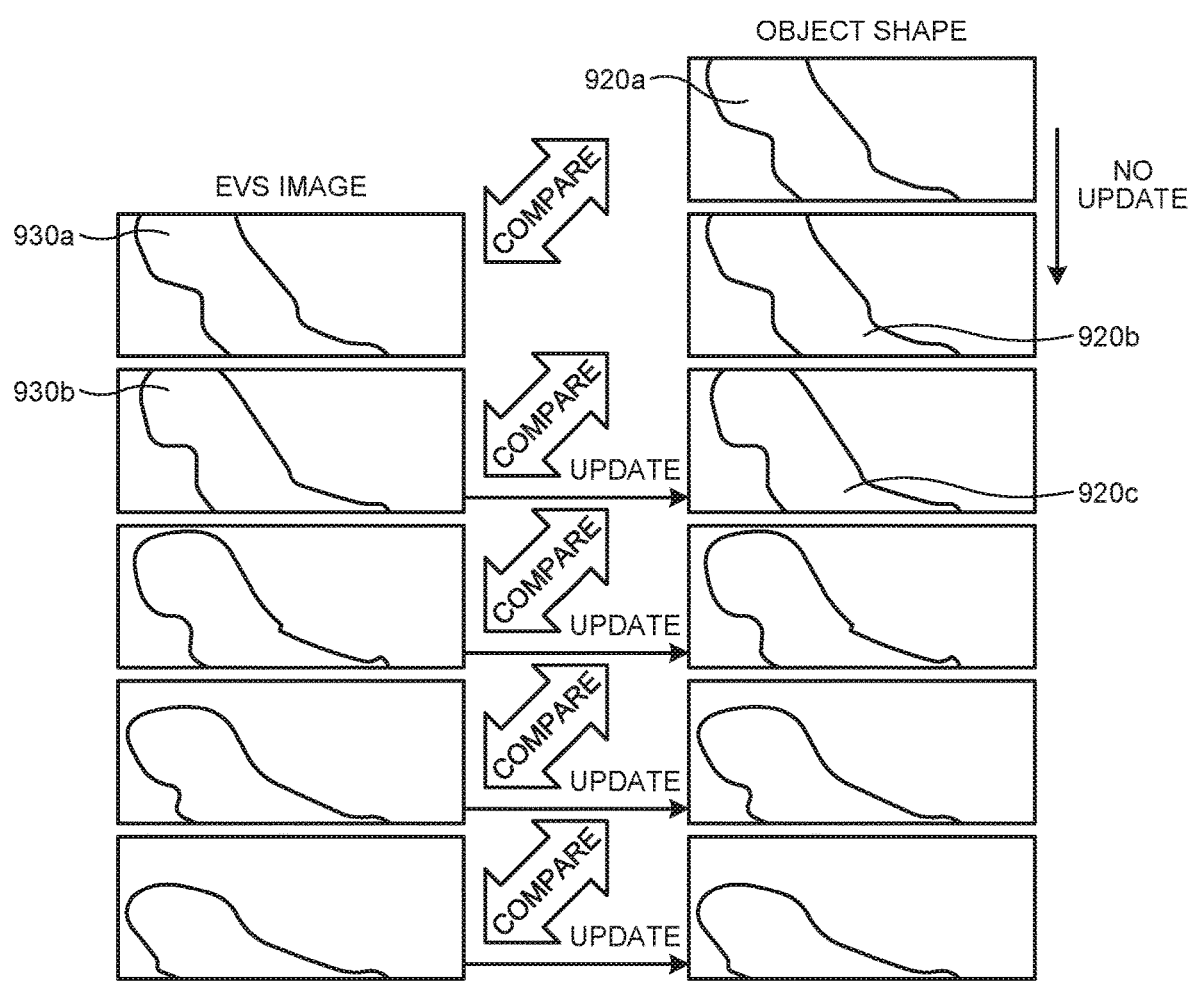
FIG. 18 is an explanatory view for describing an image recognition method according to the second example of the fourth embodiment of the present disclosure.

Furthermore, shapes of soft objects such as organs often change, and therefore it is difficult to track these soft organs by image recognition. Therefore, an example of recognition and tracking where a shape change can be captured by combining the RGB sensor 250 and the EVS 200 will be described with reference to FIGS. 17 and 18. FIG. 17 is a flowchart of the image recognition method according to the second example of the present embodiment, and FIG. 18 is an explanatory view for describing the image recognition method according to the second example of the present embodiment.

As illustrated in FIG. 17, the image recognition method according to the present example can mainly include steps of step S301 to step S307. Details of these respective steps according to the present example will be described below.

First, the medical observation system 10 recognizes a target tumor in the RGB image (step S301). Furthermore, the medical observation system 10 acquires the shape of the target tumor in the RGB image (step S302). For example, the acquired shape is an object shape 920*a* illustrated on the right side of FIG. 18.

Next, the medical observation system 10 acquires, from an EVS image, shape information (edge information) of a shape similar to the shape acquired in step S302 (step S303). For example, the shape acquired from the EVS image is an object shape 930*a* illustrated on the left side of FIG. 18.

Furthermore, the medical observation system 10 compares the detected shape information (edge information) with the shape information (edge information) of a previous frame, and determines whether or not the shape of the tumor has changed (step S304). More specifically, the object shape 920*a* in FIG. 18 and the object shape 930*a* are compared. The medical observation system 10 proceeds to step S305 in a case where the shape has changed (step S304: Yes), and proceeds to step S306 in a case where the shape has not changed (step S304: No).

Next, the medical observation system 10 updates the shape of the tumor (step S305). Here, in a case where the shape has changed from the edge information obtained from the EVS image, processing of updating the shape of the tumor is performed as needed. By repeating this processing, it is possible to track the tumor while capturing the shape change. More specifically, as illustrated in FIG. 18, for example, an object shape 920*b* that is based on the RGB image and an object shape 930*b* that is newly acquired from the EVS image one frame after the RGB image are compared to update as an object shape 920*c* the object shape that is based on the RGB image in the case where the shape has changed.

Furthermore, the medical observation system 10 determines whether or not an RGB image has been newly imported (step S306). The medical observation system 10 proceeds to step S307 in a case where the RGB image has been newly imported (step S306: Yes), and returns to above-described step S303 in a case where the RGB image has not been imported (step S306: No).

Furthermore, the medical observation system 10 performs tumor image recognition on the newly imported RGB image using a tracking result of the EVS 200 (step S307).

In the present second example, even when the shape changes, high robustness for detecting a subject that moves fast and high time resolution that are features of the EVS 200 make it possible to track the tumor position highly accurately at a high speed. Note that, in the present second example, the shape of the tumor changes, and therefore a shape of an ROI may also be deformed according to the shape of the tumor.

7. Fifth Embodiment

By the way, although a method for averaging or synthesizing images in a time direction is conceived to suppress a noise amount of the images, if a position of a subject is not correctly adjusted, image quality deteriorates. Although, in a case where a conventional RGB image is used, a motion amount of a tumor is obtained using RGB images of preceding and subsequent frames, and the position of the subject is adjusted based on a motion amount of the subject, there is a limit in increasing a frame rate, and therefore when the subject moves at a high speed, it is difficult to accurately obtain the motion amount of the subject, and accurately adjust the position of the subject in some cases.

Hence, in the fifth embodiment of the present disclosure, it is possible to accurately obtain the motion amount of the subject by combining an RGB sensor 250 and an EVS 200.

Figure 19:
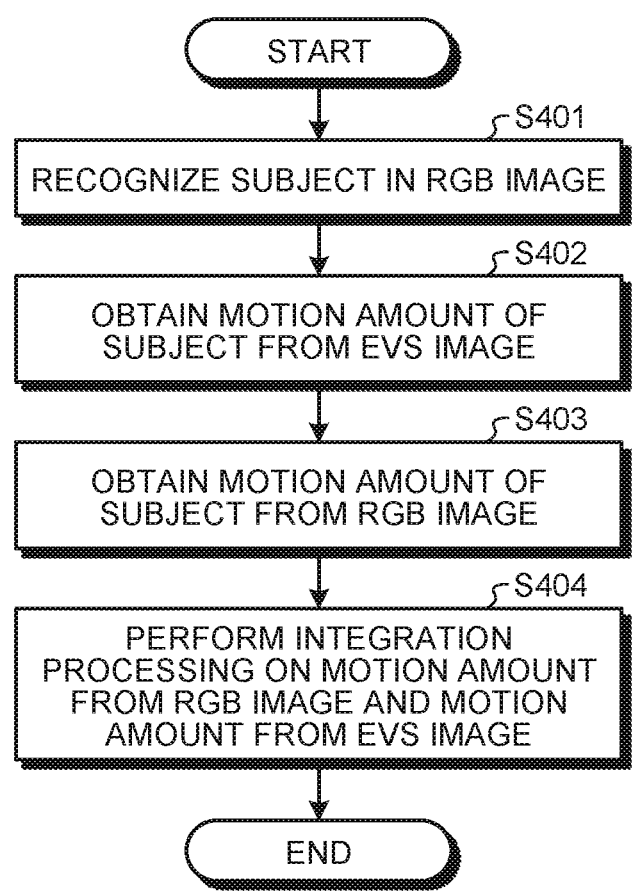
FIG. 19 is a flowchart of an image recognition method according to a fifth embodiment of the present disclosure.

As a result, in the present embodiment, it is possible to accurately adjust the position of the subject based on the motion amount of the subject, and consequently achieve a highly accurate noise suppression effect. Hereinafter, the present embodiment will be described with reference to FIGS. 19 and 20. FIG. 19 is a flowchart of an image recognition method according to the present embodiment, and FIG. 20 is an explanatory view for describing the present embodiment.

As illustrated in FIG. 19, the image recognition method according to the present embodiment can mainly include steps of step S401 to step S404. Details of these respective steps according to the present embodiment will be described below.

Figure 20:
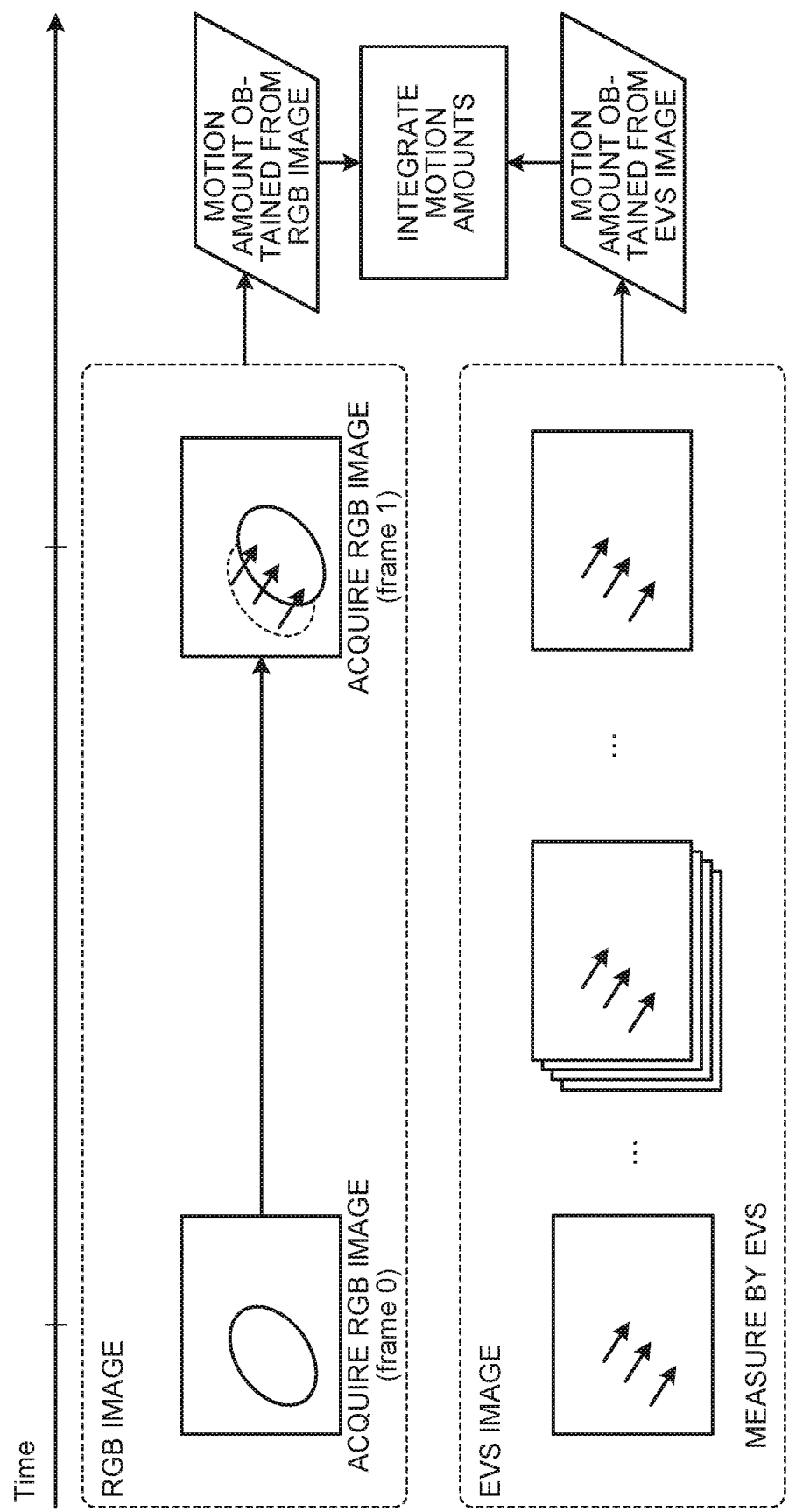
FIG. 20 is an explanatory view for describing the fifth embodiment of the present disclosure.

First, as illustrated on the left side of the upper part of FIG. 20, a medical observation system 10 acquires an RGB image (frame 0) of the RGB sensor 250, and recognizes a subject (step S401). Furthermore, as illustrated in the lower part of FIG. 20, the medical observation system 10 obtains a motion amount of the subject using continuously acquired EVS images based on the recognized subject (step S402).

Next, as illustrated on the right side of the upper part of FIG. 20, the medical observation system 10 obtains the motion amount of the subject using the already acquired RGB image (frame 0) and an RGB image (frame 1) newly acquired by the RGB sensor 250 (step S403). Furthermore, the medical observation system 10 can obtain the accurate motion amount of the subject by integrating and processing the motion amount from the RGB image and the motion amount from the EVS image (step S404).

Note that, in the present embodiment, when the image is dark or when the motion of the subject is fast, the motion amount from the EVS image may be weighted highly compared to the motion amount from the RGB image to calculate a final motion amount of the subject. Furthermore, in the present embodiment, when the image is bright or when the motion of the subject is slow, the motion amount from the RGB image may be weighted highly compared to the motion amount from the EVS image to calculate the final motion amount of the subject.

8. Conclusion

As described above, according to each embodiment of the present disclosure, it is possible to robustly and highly accurately measure and recognize a subject in real time.

Note that, in the above-described embodiments of the present disclosure, an imaging target is not limited to an inside of an abdominal cavity, may be living body tissues, a fine mechanical structure, or the like, and is not particularly limited. Furthermore, the above-described embodiments of the present disclosure are not limited to application to medical use, research use, or the like, and can be applied to an observation device that performs, for example, highly accurate analysis using an image. Consequently, the above-described medical observation system 10 can be used as an observation system (observation device).

Furthermore, the above-described medical observation system 10 can be used as a rigid endoscope, a flexible endoscope, an exoscope, a microscope, or the like, and may not include a robot arm 800 or may include only the EVS 200, and a configuration thereof is not particularly limited, either.

9. Hardware Configuration

Figure 21:
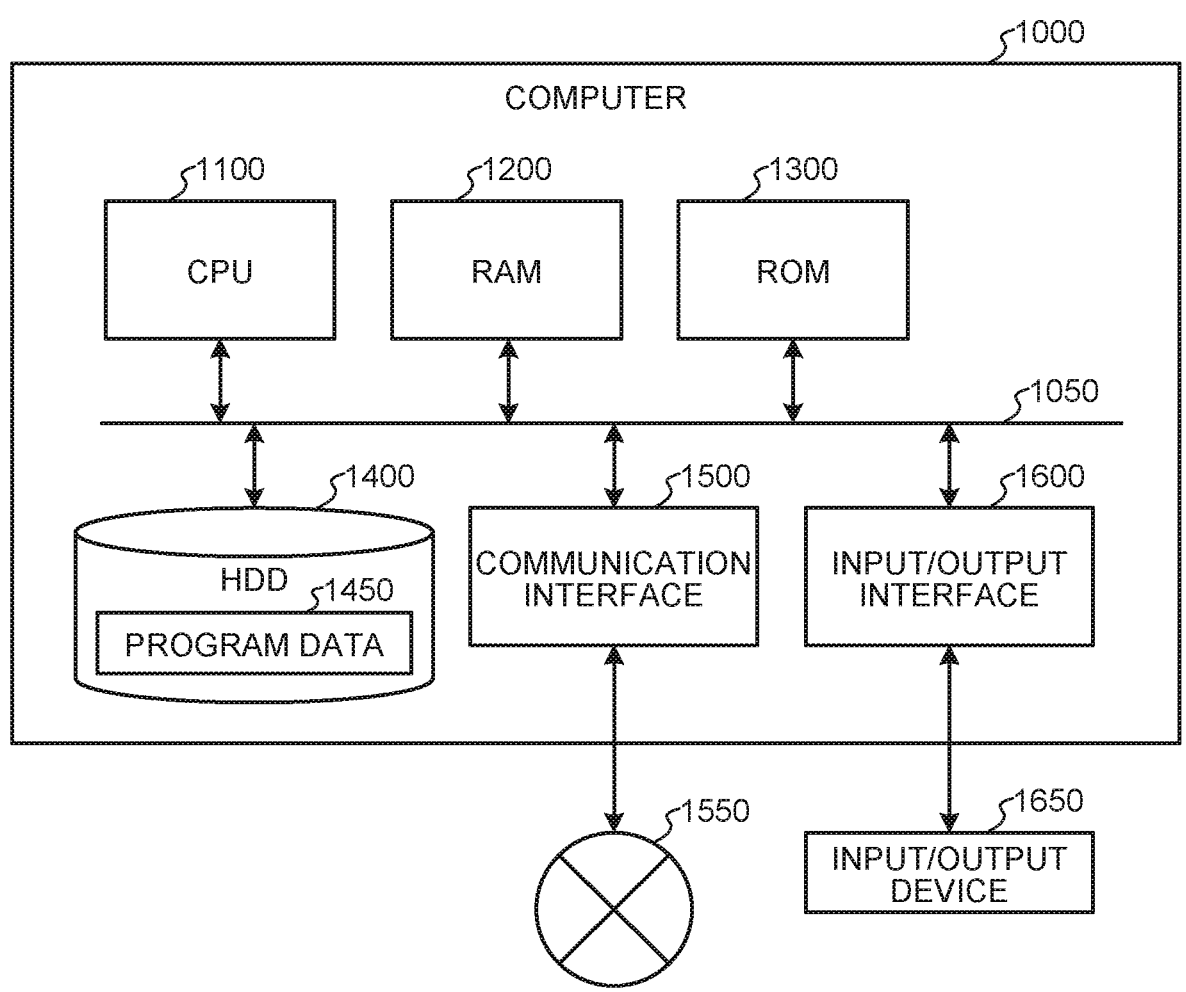
FIG. 21 is a hardware configuration diagram illustrating an example of a computer that implements a CCU 500 according to the embodiments of the present disclosure.

An information processing device such as a CCU 500 according to each of the above-described embodiments is realized by, for example, a computer 1000 employing a configuration illustrated in FIG. 21. Hereinafter, the CCU 500 according to the embodiments of the present disclosure will be described as an example. FIG. 21 is a hardware configuration diagram illustrating an example of a computer that implements the CCU 500 according to the embodiments of the present disclosure. The computer 1000 includes a CPU 1100, a RAM 1200, a Read Only Memory (ROM) 1300, a Hard Disk Drive (HDD) 1400, a communication interface 1500, and an input/output interface 1600. Each unit of the computer 1000 is connected by a bus 1050.

The CPU 1100 operates based on a program stored in the ROM 1300 or the HDD 1400, and controls each unit. For example, the CPU 1100 develops in the RAM 1200 a program stored in the ROM 1300 or the HDD 1400, and executes processing corresponding to various programs.

The ROM 1300 stores a boot program such as a Basic Input Output System (BIOS) executed by the CPU 1100 when the computer 1000 is activated, a program that depends on hardware of the computer 1000, and the like.

The HDD 1400 is a computer-readable recording medium that non-transiently records a program executed by the CPU 1100, data used by this program, and the like. More specifically, the HDD 1400 is a recording medium that records a program for the medical observation system 10 according to the present disclosure that is an example of program data 1450.

The communication interface 1500 is an interface for the computer 1000 to connect to an external network 1550 (e.g., the Internet). For example, the CPU 1100 receives data from another equipment, and transmits data generated by the CPU 1100 to the another equipment via the communication interface 1500.

The input/output interface 1600 is an interface for connecting an input/output device 1650 and the computer 1000. For example, the CPU 1100 receives data from an input device such as a keyboard and a mouse via the input/output interface 1600. Furthermore, the CPU 1100 transmits data to an output device such as a display, a speaker, or a printer via the input/output interface 1600. Furthermore, the input/output interface 1600 may function as a media interface that reads a program or the like recorded on computer-readable predetermined recording media (media). The media are, for example, optical recording media such as a Digital Versatile Disc (DVD) and a Phase change rewritable Disk (PD), magneto-optical recording media such as a Magneto-Optical disk (MO), tape media, magnetic recording media, semiconductor memories, or the like.

For example, in a case where the computer 1000 functions as the CCU 500 according to the embodiments of the present disclosure, the CPU 1100 of the computer 1000 realizes a function of controlling the medical observation system 10 by executing a program loaded on the RAM 1200. Furthermore, the HDD 1400 may store the program for controlling the medical observation system 10 according to the embodiments of the present disclosure. Note that, although the CPU 1100 reads the program data 1450 from the HDD 1400 to execute, the information processing program may be acquired from another device via the external network 1550 in another example.

Furthermore, the CCU 500 according to the present embodiment may be applied to a system including a plurality of devices that assumes connection to a network (or communication between respective devices) such as cloud computing.

An example of the hardware configuration of the CCU 500 has been described above. Each of the above-described components may be configured using a general-purpose part, or may be configured by hardware specialized in the function of each component. Such a configuration can be appropriately changed according to technical levels at times of implementation.

10. Supplementary Note

Note that the embodiments of the present disclosure described above can include, for example, an information processing method executed by the above-described medical observation system 10, a program for causing the medical observation system 10 to function, and a non-transitory tangible medium in which the program is recorded. Furthermore, the program may be distributed via a communication line (including wireless communication) such as the Internet.

Furthermore, each step of the information processing method according to the above-described embodiments of the present disclosure may not necessarily be processed in the described order. For example, the order of each step may be appropriately changed to perform processing. Furthermore, each step may be processed partially in parallel or individually instead of being processed in chronological order. Furthermore, the processing of each step does not necessarily need to be performed according to the described method, and may be performed by, for example, another method by another functional unit.

It is possible to manually perform all or part of processing described as the processing that is automatically performed among each processing described in each of the above embodiments, or automatically perform by a known method all or part of processing described as the processing that is manually performed. Furthermore, the processing procedures, the specific names, and information including the items of various data and parameters illustrated in the above description and drawings can be arbitrarily changed unless otherwise specified. For example, the various pieces of information illustrated in each drawing are not limited to the illustrated information.

Furthermore, each component of each device illustrated in the drawings is functionally conceptual, and does not necessarily need to be physically configured as illustrated in the drawings. That is, the specific modes of distribution and integration of each device are not limited to the illustrated modes, and all or part thereof can be functionally or physically distributed and integrated in an arbitrary unit according to various loads, usage conditions, and the like.

Although the preferred embodiments of the present disclosure have been described in detail with reference to the accompanying drawings, the technical scope of the present disclosure is not limited to these embodiments. It is obvious that a person having common knowledge in the technical field of the present disclosure can arrive at various modified examples or altered examples within the scope of the technical idea recited in the claims, and it is naturally understood that these modified examples or altered examples also belong to the technical scope of the present disclosure.

Furthermore, the effects described in the description are merely illustrative or exemplary, and are not restrictive. That is, the technique according to the present disclosure can exhibit other effects that are obvious to those skilled in the art from the disclosure of the description together with the above effects or instead of the above effects.

Note that the technique of the present disclosure can also employ the following configurations.

(1) A medical observation device comprising an imaging unit that can image an environment inside an abdominal cavity of a living body,
wherein the imaging unit includes
a plurality of first pixels that are aligned in a matrix, and
an event detection unit that detects that a luminance change amount of light incident on each of the plurality of first pixels exceeds a predetermined threshold.

(2) The medical observation device according to (1), further comprising a medical light source that irradiates the inside of the abdominal cavity with the light.

(3) The medical observation device according to (1) or (2), wherein the environment inside the abdominal cavity is at least one of a tumor, a surgical site, and a surgical instrument.

(4) The medical observation device according to (2), further comprising
an image detection unit that includes a plurality of second pixels that are aligned in a matrix, and detects an image that is based on the light incident on each of the plurality of second pixels.

(5) The medical observation device according to (4), wherein the imaging unit is provided in a distal end part inserted in the inside of the abdominal cavity.

(6) The medical observation device according to (4), further comprising
a dispersion unit that guides the light to the imaging unit and the image detection unit.

(7) The medical observation device according to (4), wherein the plurality of first pixels or the plurality of second pixels are disposed on a same light reception surface.

(8) The medical observation device according to (4), further comprising an adjustment unit that adjusts a frame rate of an image obtained by the imaging unit.

(9) The medical observation device according to (4), further comprising a distribution ratio adjustment unit that adjusts a distribution ratio of a light quantity of the incident light between the imaging unit and the image detection unit.

(10) The medical observation device according to any one of (4) to (9), wherein an angle of view of a scene captured by the imaging unit is different from an angle of view of a scene captured by the image detection unit.

(11) The medical observation device according to any one of (1) to (10), further comprising a drive unit that moves the plurality of first pixels along a predetermined direction.

(12) The medical observation device according to (1), further comprising:
an optical system that takes in light into the imaging unit; and
a drive unit that moves the optical system along a predetermined direction.

(13) The medical observation device according to (4), further comprising a processing unit that processes a first output from the imaging unit, and a second output from the image detection unit.

(14) The medical observation device according to (13), wherein
the processing unit recognizes a subject based on the first and second outputs.

(15) The medical observation device according to (13), wherein the processing unit
specifies a subject based on the second output; and
tracks the subject based on the first output.

(16) The medical observation device according to (13), wherein the processing unit
calculates a motion of a subject based on the first and second outputs.

(17) The medical observation device according to (13), wherein
the imaging unit is provided in a camera head unit, and
the medical observation device further comprises a robot arm that supports the camera head unit.

(18) The medical observation device according to (17), further comprising another robot arm that supports a surgical instrument.

(19) The medical observation device according to (17), further comprising a control unit that performs control to cause the robot arm to autonomously operate based on a processing result of the processing unit.

(20) The medical observation device according to any one of (1) to (19), wherein medical observation device is one of an endoscope, an exoscope, and a microscope.

(21) An observation device comprising:
an imaging unit; and
an image detection unit, wherein
the imaging unit includes a plurality of first pixels that are aligned in a matrix, and an event detection unit that detects that a luminance change amount of light incident on each of the plurality of first pixels exceeds a predetermined threshold, and
the image detection unit includes a plurality of second pixels that are aligned in a matrix, and detects an image that is based on the light incident on each of the plurality of second pixels.

(22) The observation device according to (21), wherein an angle of view of a scene captured by the imaging unit is different from an angle of view of a scene captured by the image detection unit.

(23) The observation device according to (21) or (22), further comprising an adjustment unit that adjusts a frame rate of an image obtained by the imaging unit.

(24) An observation method comprising: by a medical observation device that can image an environment inside an abdominal cavity of a living body:
detecting luminance of light incident on each of a plurality of first pixels aligned in a matrix;
calculating a change amount of the luminance; and
determining whether or not the change amount exceeds a predetermined threshold.

(25) An adapter that comprises a plurality of second pixels aligned in a matrix, and is inserted between a camera head unit and an optical system, the camera head unit including an image detection unit that detects an image that is based on light incident on each of the plurality of second pixels, and the optical system guiding the light to the camera head unit, the adapter comprising
an imaging unit that can image an environment inside an abdominal cavity of a living body,
wherein the imaging unit includes
a plurality of first pixels that are aligned in a matrix, and
an event detection unit that detects that a luminance change amount of light incident on each of the plurality of first pixels exceeds a predetermined threshold.

REFERENCE SIGNS LIST

10 MEDICAL OBSERVATION SYSTEM
100, 100a CAMERA HEAD
102, 502, 522, 532, 602, 702 COMMUNICATION UNIT
150 ADAPTER
200 EVS
211 DRIVE CIRCUIT
212 SIGNAL PROCESSING UNIT
213 ARBITER UNIT
214 COLUMN PROCESSING UNIT
250 RGB SENSOR
260 PRISM
270 ACTUATOR
300 PIXEL ARRAY UNIT
302 PIXEL
304 LIGHT RECEPTION UNIT
306 PIXEL SIGNAL GENERATION UNIT
308 DETECTION UNIT
310 PERIPHERAL CIRCUIT UNIT
316 DRIVE CONTROL UNIT
400 OPTICAL SYSTEM
410 OPTICAL UNIT
500 CCU
504 RGB SIGNAL/IMAGE PROCESSING UNIT
506 RGB RECOGNITION UNIT
508 INTEGRATION INFORMATION PROCESSING/CONTROL UNIT
514 EVENT PREPROCESSING UNIT
516 EVENT INFORMATION PROCESSING UNIT
520 SYNCHRONIZATION CONTROL UNIT
530 DISPLAY INFORMATION GENERATION UNIT
540 EVS FRAME ADJUSTMENT UNIT
542 FRAME RATE ADJUSTMENT UNIT
600 LIGHT SOURCE DEVICE
604 LIGHT SOURCE CONTROL UNIT
606 LIGHT SOURCE UNIT
700 ROBOT CONTROL UNIT
704 ARM TRAJECTORY GENERATION UNIT
706 ARM CONTROL UNIT
800 ROBOT ARM
802 ARM ACTUATOR
900 DISPLAY DEVICE
910a, 910b SURGICAL INSTRUMENT
920a, 920b, 920c, 930a, 930b OBJECT SHAPE

The invention claimed is:

1. A medical observation device, comprising:
a first image sensor that includes a plurality of first pixels in a first matrix;
a second image sensor that includes a plurality of second pixels in a second matrix;
a medical light source configured to irradiate inside of an abdominal cavity of a living body with light;
each of the first image sensor and the second image sensor is configured to receive the light from the abdominal cavity; and
a prism configured to adjust a distribution ratio between a light quantity of the light received by the first image sensor and a light quantity of the light received by the second image sensor, wherein
the first image sensor is further configured to:
detect, based on the adjustment of the distribution ratio, a change in luminance of the light received by each pixel of the plurality of first pixels, wherein the change in the luminance is greater than a threshold; and
capture, based on the detected change, an image of an environment of the inside of the abdominal cavity, and
the second image sensor is further configured to capture, based on the light received by each pixel of the plurality of second pixels, an image of a surgical site of the living body.

2. The medical observation device according to claim 1, wherein
the first image sensor is in a distal end part of the medical observation device, and the distal end part is insertable in the inside of the abdominal cavity.

3. The medical observation device according to claim 1, wherein the prism is further configured to:
receive the light form the abdominal cavity; and
guide the light received from the abdominal cavity to the first image sensor and the second image sensor.

4. The medical observation device according to claim 1, further comprising a central processing unit (CPU) configured to adjust a frame rate of the image captured by the first image sensor.

5. The medical observation device according to claim 1, wherein
the first image sensor is further configured to capture a first scene at a first angle of view,
the second image sensor is further configured to capture a second scene at a second angle of view,
the second angle of view is different from the first angle of view, and
the first scene corresponds to the environment of the inside of the abdominal cavity and the second scene corresponds to the surgical site of the living body.

6. The medical observation device according to claim 1, further comprising a central processing unit (CPU) configured to:
process a first output of the image of the environment of the inside of the abdominal cavity; and
process a second output of the image of the surgical site of the living body.

7. The medical observation device according to claim 6, wherein the CPU is further configured to recognize a subject based on the first output and the second output.

8. The medical observation device according to claim 6, wherein the CPU is further configured to:
recognize a subject based on the first output; and
track the subject based on the second output.

9. The medical observation device according to claim 6, wherein the CPU is further configured to calculate a motion of a subject based on the first output and the second output.

10. The medical observation device according to claim 6, further comprising a first robot arm configured to support the first image sensor.

11. The medical observation device according to claim 10, further comprising a second robot arm configured to support a surgical instrument.

12. The medical observation device according to claim 10, wherein the CPU is further configured to control, based on the first output and the second output, an autonomous operation of the first robot arm.

13. The medical observation device according to claim 1, wherein the environment is at least one of a tumor, the surgical site, or a surgical instrument.

14. The medical observation device according to claim 1, further comprising an actuator configured to move the plurality of first pixels along a specific direction.

15. The medical observation device according to claim 1, further comprising:
an optical system configured to:
receive the light from the abdominal cavity; and
guide the light received from the abdominal cavity into the first image sensor; and
an actuator configured to move the optical system along a specific direction.

16. The medical observation device according to claim 1, wherein the medical observation device is one of an endoscope, an exoscope, or a microscope.

17. An observation device, comprising:
a first image sensor that includes a plurality of first pixels in a first matrix, wherein
the first image sensor is configured to:
receive light by each pixel of the plurality of first pixels;
detect a change in luminance of the light received by each pixel of the plurality of first pixels, wherein the change in the luminance is greater than threshold; and
capture, based on the detected change, a first scene at a first angle of view; and
a second image sensor that includes a plurality of second pixels in a second matrix, wherein
the second image sensor is configured to:
receive the light by each pixel of the plurality of second pixels; and
capture, based on the light received by each pixel of the plurality of second pixels, a second scene at a second angle of view, and
the second angle of view is different from the first angle of view.

18. The observation device according to claim 17, further comprising a central processing unit (CPU) configured to adjust a frame rate of the first scene captured by the first image sensor.

19. An observation method, comprising:
in a medical observation device that includes a first image sensor, a second image sensor, a medical light source, a prism, and a central processing unit (CPU):
irradiating, by the medical light source, inside of an abdominal cavity of a living body with light;
receiving, by each of the first image sensor and the second image sensor, the light from the abdominal cavity;
adjusting, by the prism, a distribution ratio between a light quantity of the light received by the first image sensor and a light quantity of the light received by the second image sensor;
detecting, by the first image sensor, luminance of the light received by each pixel of a plurality of first pixels, wherein
the luminance is detected based on the adjustment of the distribution ratio, and
the first image sensor includes the plurality of first pixels in a first matrix;
calculating, by the first image sensor, a change in the detected luminance;
determining, by the first image sensor, the change in the luminance is greater than a threshold;
capturing, by the first image sensor, based on the determination that the change in the luminance is greater than the threshold, an image of an environment of the inside of the abdominal cavity; and
capturing, by the second image sensor, based on the light received by each pixel of a plurality of second pixels, an image of a surgical site of the living body, wherein the second image sensor includes the plurality of second pixels in a second matrix.

* * * * *